United States Patent [19]
Darveau

[11] Patent Number: 5,840,302
[45] Date of Patent: Nov. 24, 1998

[54] TREATMENT OF BACTERIALLY-INDUCED INFLAMMATORY DISEASES

[75] Inventor: Richard P. Darveau, Kirkland, Wash.

[73] Assignee: Bristol-Myers Squibb Company, New York, N.Y.

[21] Appl. No.: 337,614

[22] Filed: Nov. 10, 1994

Related U.S. Application Data

[63] Continuation-in-part of Ser. No. 150,635, Nov. 10, 1993, abandoned.

[51] Int. Cl.[6] ........................ A61K 39/40; A61K 39/395; A61K 38/46; C07K 16/00
[52] U.S. Cl. ..................................... 424/150.1; 424/136.1; 424/164.1; 424/178.1; 424/94.6; 514/1; 435/197; 435/195; 530/388.4
[58] Field of Search ............................. 424/150.1, 94.6, 424/136.1, 146.1, 178.1; 530/388.4; 514/1; 435/197, 195

[56] References Cited

U.S. PATENT DOCUMENTS

| | | |
|---|---|---|
| 2,944,941 | 7/1960 | Goldenberg . |
| 4,661,350 | 4/1987 | Tsurumizu et al. . |
| 4,689,221 | 8/1987 | Kiyoshige et al. ........................ 424/87 |
| 5,013,661 | 5/1991 | Munford et al. . |

FOREIGN PATENT DOCUMENTS

| | | |
|---|---|---|
| 148025 | 7/1985 | European Pat. Off. . |
| 0269388 | 1/1988 | European Pat. Off. . |
| 269388 | 6/1988 | European Pat. Off. . |
| 91/03556 | 3/1991 | European Pat. Off. . |
| 92/07086 | 4/1992 | European Pat. Off. . |
| 61-140527 | 6/1986 | Japan . |
| 1-313438 | 12/1989 | Japan . |
| 2-135096 | 5/1990 | Japan . |
| 2151923 | 7/1985 | United Kingdom . |
| 9109967 | 7/1991 | WIPO . |
| 92/0444 | 3/1992 | WIPO . |

OTHER PUBLICATIONS

Skare et al., "Energy Transduction Between Membranes", *J. Biol. Chem.* 268: 16302–16308 (Aug. 5, 1993).

Grober et al., "Monocyte–endothelial Adhesion in Chronic Rheumatoid Arthritis," *J. Clin. Invest.* 91:2609–2619 (1993).

Sjostrum et al., "Effect of Treatment on Titer, Function, and Antigen Recognition of Serum Antibodies to Actinobacillus Actinomycetemcomitans in Patients with Rapidly Progressive Periodontitis", *Infect. Immun.* 62:145–151 (Jan., 1994).

Persson et al., "Immunization against Porphyromonas Gingivalis Inhibits Progression of Experimental Periodontitis in Nonhuman Primates", *Infect. Immun.,* 62:1026–1031 (Mar., 1994).

Bailey, et al., "Serial Recloning of SV40 Early Gene Transfected Human Endothelial Cells Repeatedly Recovers Subpopulations with Low Passage Characteristics and Morphologies," *Biochem. Cell Biol.,* 72:117–125 (1994).

Darveau, et al., "Ability of Bacteria Associated with Chronic Inflammatory Disease to Stimulate E–Selectin Expression and Promote Neutrophil Adhesion," *Infect. Immun.* 63:1311–1317 (1995).

Ranney et al., "Relationship Between Attachment Loss and Precipitating Serum Antibody to Actinobacillus Actinomycetemcomitans in Adolescents and Young Adults Having Severe Periodontal Destruction", *J. Periodontal.* 53:1–7 (Jan., 1982).

Darveau and Hancock, "Procedure for Isolation of Bacterial Lipopolysaccharides from Both Smooth and Rough Pseudomonas Aeruginosa and Salmonella Typhimurium Strains",*J. Bacteriol.* 155: 831–838 (Aug., 1983).

Anderson et al., "The Severe and Moderate Phenotypes of Heritable Mac–1, LFA–1 Deficiency", *J. Infect. Dis.* 152:668–689 (Oct., 1985).

Socransky et al., "Frequency Distributions of Periodontal Attachment Loss", *J. Clin. Periodontal.* 13: 617–624 (1986).

Pohlman et al., "Deacylated Lipopolysaccaride Inhibits Neutrophil Adherence to Endothelium Induced by Lipopolysaccharide in vitro," *J. Exp. Med.,* 165:1393–1402 (1987).

Gunsolley et al., "Relationship of Serum Antibody to Attachment Level Patterns in Young Adults with Juvenile Periodontitis or Generalized Severe Periodontitis", *J. Periodontal.* 58: 314–320 (May, 1987).

Holt et al., "Implantation of Bacteroides Gingivalis in Nonhuman Primates Initiates Progression of Periodintitis", *Science* 239: 55–57 (Jan. 1, 1988).

Bevilacqua et al., "Endothelial Leukocyte Adhesion Molecule 1", *Science* 243: 1160–1165 (Mar. 3, 1989).

Johnston et al., "Cloning of GMP–140, a Granule Membrane Protein of Platelets and Endothelium", *Cell* 56: 1033–1044 (Mar. 24, 1989).

McArthur et al., "Modulation of Colonization by Black–Pigmented Bacteroides Species in Squirrel Monkeys by Immunization with Bacteroides Gingivalis", *Infect. Immun.* 57: 2313–2317 (Aug., 1989).

Magnuson et al., "Human Endothelial Cell Adhesiveness for Neutrophilis, Induced by *Escherichia coli* Lipopolysaccharide in vitro, is inhibited by Bacteroides Fragilis Lipopolysaccaride", *J. Immunol.* 143:3025–3030 (Nov. 1, 1989).

(List continued on next page.)

*Primary Examiner*—Susan A. Loring
*Attorney, Agent, or Firm*—Townsend and Townsend and Crew LLP

[57] ABSTRACT

The lipopolysaccharide of bacteria associated with chronic inflammatory diseases is unable to induce expression of leukocyte adhesion molecules, or selectins, on endothelial cells, and is also capable of inhibiting the induction of selectin expression by bacteria normally associated with acute endotoxin disease. New approaches to treatment of these diseases, and the diagnosis of susceptibility to chronic bacterial-associated inflammatory diseases, are provided.

13 Claims, 13 Drawing Sheets

OTHER PUBLICATIONS

Huse et al., "Generation of a Large Combinatorial Library of the Immunoglobulin Repertoire in Phage Lambda", *Science* 246:1275–1281 (Dec. 8, 1989).

Klausen, "Microbiological and Immunological Aspects of Experimental Periodontal Disease in Rats", *J. Periodontal,* 62:59–73 (Jan., 1991).

Clark et al., "Immune Modulation of Prevotella Intermedia Colonization in Squirrel Monkeys", *Infect. Immun.,* 59:1927–1931 (Jun., 1991).

Waldmann, "Monoclonal Antibodies in Diagnosis and Therapy," *Science,* 252:1657–1662 (Jun., 1991).

Ebersole et al., "Effects of Immunization with Porphyromonas Gingivalis and Prevotella Intermedia on Progression on Ligature–Induced Periodontitis in the Nonhuman Primate Macaca Fascicularis", *Infect. Immun.* 59:3351–3359 (Oct., 1991).

Chen et al., "Humoral Immune Responses to Porphyromonas Gingivalis Before and Following Therapy in Rapidly Progressive Periodontitis Patients", *J. Periodontal.* 62:781–791 (Dec., 1991).

Ebersole, "Systemic Antibody Responses to oral Microorganisms in the Cynomolgus Monkey: Development of Methodology and Longitudinal Responses During Ligature––Induced Disease," *Res. Immunol.,* 142:829–839 (1991).

Page, R. C., "The Role of Inflammatory Mediators in the Pathogenesis of Periodontal Disease," *J. Periodont. Res.* 26:230–242 (1991).

Frey et al., "Soluble CD14 Participates in the Response of Cells to Lipopolysaccharide", *J. Exp. Med.* 176: 1665–1671 (1992).

Kesavalu et al., "Porphyromonas Gingivalis Virulence in Mice", *Infect. Immun.* 60:1455–1464 (Apr., 1992).

Socransky et al., "The Bacterial Etiology of Destructive Periodontal Disease", *J. Periodontal.* 63: 322–331 (Apr., 1992).

Genco et al., "Influence of Immunization on Porphyromonas Gingivalis Colonization and Invasion in the Mouse Chamber Model", *Infect. Immun.,* 60:1447–1454 (Apr., 1992).

Evans et al., "Immunization with Porphyromonas (Bacteroides) Gingivalis Fimbriae Protects Against Periodontal Destruction", *Infect. Immun.* 60:2926–2935 (Jul. 1992).

Lasky, "Selectins: Interpreters of Cell–Specific Carbohydrate Information During Inflammation", *Science* 258: 964–969 (Nov. 6, 1992).

Etzioni et al., "Recurrent Severe Infections Caused by a Novel Leukocyte Adhesion Deficiency", *N. Engl. J. Med.* 327: 1789–1792 (Dec. 17, 1992).

Fitzer–Schiller, "Centocor Stops Trials of Flagship Drug," *The Washington Post,* D3, (Jan., 1993).

Stone, "Dental Institute Looks for Big Changes," *Science* 259:1243 (Feb., 1993).

Spaulding, "In Shocking Synergen, Sepsis Tallies Third Victim," *Biotechnology,* 11:428–429, Apr. 1993.

Pugin et al., "Lipopolysaccharide Activation of Human Endothelial cells and Epithelail in Mediated by Lipopolysaccharide–binding protein and Soluble CD14" *Proc. Natl. Acad. Sci. USA* 90: 2744–2748 (Apr., 1993).

Ou et al. (1993) *Prog. Abstr. Ann. Mtg. Intl Assoc. Dent. Res.,* Abst. No. 2416.

Darveau et al., (1995) *Infect. Immun.* 63 (4) : 1311–1317.

Naito, Y et al, Infection & Immunity, 50(1):231–235, Oct. 1985.

Shelburne, C.E., J. Period Res., 28:1–9, 1993. (Jan.).

Remington's Pharmaceutical Sciences, p. 821, 1989.

Yu–Chang, John Wang et al, J. Parenteral Drug Assoc, 34(6):452–462, Nov.–Dec. 1980.

- *E. coli*
- ○ *P. gingivalis* (33277)
- △ *P. gingivalis* (A7A1-28)
- ▲ *P. gingivalis* (5083)
- □ *B. forsythus*

TREATMENT OF BACTERIALLY-INDUCED INFLAMMATORY DISEASES

RELATED APPLICATION

This is a continuation-in-part of Ser. No. 08/150,635, filed on Nov. 10, 1993, now abandoned, which is expressly incorporated herein by reference.

BACKGROUND OF THE INVENTION

This invention relates generally to methods for treating and preventing periodontal diseases. Periodontal diseases are inflammatory disorders of the tissues supporting the teeth. These tissues are collectively referred to as the periodontium and include the gingiva, periodontal ligament, root cementum, and alveolar bone. Inflammation of the periodontium is the major cause of tooth loss in the adult population in most countries.

Periodontal diseases generally encompass two major and distinct subclasses of disease, gingivitis and periodontitis. Gingivitis is characterized by inflammation of the gingiva without bone loss or loss of connective tissue attachment. Gingivitis is caused by bacterial accumulation in the crevicular spaces. The gingiva becomes inflamed without spread to surrounding tooth support structures. Gingivitis may be graded by severity, with mild gingivitis diagnosed clinically by erythema at the sites of inflammation. Moderate gingivitis involves bleeding of the gingiva upon gentle probing, and severe gingivitis is characterized by a tendency for spontaneous gingival bleeding. Gingivitis is a precondition for, but does not necessarily lead to, periodontitis.

Periodontitis is an inflammatory disorder that can involve all tissues of the periodontium. In periodontitis, oral bacteria accumulate at the junction of the teeth and gingiva causing inflammation of the local periodontal tissues. The inflammation degrades the collagen fibers of the periodontal tissues, causing loss of tooth support and the progressive development of a space between the tooth and the gingiva (periodontal or gingival pocket). As the periodontitis progresses, the periodontal pockets deepen, resulting in inadequate tooth support and tooth loss.

Many patients with severe periodontitis have serum antibodies to antigens of their infecting bacteria. The role these antibodies play in the progression of periodontitis is not known, although many believe that they may be protective. Patients with high antibody titers have less severe disease and fewer affected teeth than those with low titers. Gunsolley et al., *J. Periodontol.* 58: 314–320 (1987) and Ranney et al., *J. Periodontol.* 53: 1–7 (1982). Serum antibodies in the presence of complement significantly enhance phagocytosis and killing of periodontal pathogens by neutrophils. Underwood et al., *J. Infect. Dis.* (1993), and Sjostrom et al., *Infect. Immun.* 62:145–151 (1994). Following periodontal treatment, previously seronegative patients convert, and the capacity of their sera to stimulate phagocytosis and killing by neutrophils significantly increases along with increasing antibody titers and avidities. Chen et al., *J. Periodontol.* 62: 781–791 (1991); Ou et al., *Prog. Abstr. Ann. Mtg. Intl. Assoc. Dent. Res.* abstr. 2416 (1993).

Of the vast numbers of bacterial species which occupy the gingival crevice and the developing periodontal pocket, only a small group are considered putative pathogens. Prominent among the periodontopathic microbiota is *Porphyromonas (Bacteroides) gingivalis*. *Porphyromonas gingivalis* is a gram-negative anaerobic bacillus that has been strongly implicated as an etiologic agent in adult periodontal disease. Socransky and Haffajee, *J. Periodontol.* 4: 322 (1992). Recently, in a non-human primate model of periodontal disease, the emergence of this organism from the subgingival microbiota was associated with an increase in alveolar bone loss. Holt et al., *Science* 239: 55 (1988). This data lends support to the hypothesis that a microbiological "bloom" of *P. gingivalis* may be associated with progression of the disease. Socransky and Haffajee, *J. Clin. Periodontol.* 13: 617 (1986). The relationship between the presence of *P. gingivalis* and the chronic inflammatory nature of the disease remains unclear.

One of the first steps in the inflammatory process is the emigration of leukocytes from the vascular compartment to extravascular tissues. Lasky, *Science* 258: 964 (1992). Leukocyte emigration is initiated by an inflammatory stimulus which induces the expression of selectin molecules on the surface of vascular endothelial cells. Potent inducers of selectin include *E. coli* lipopolysaccharide (LPS), tumor necrosis factor (TNF) and interleukin-1 (IL-1). An initial binding of low affinity and high avidity occurs between carbohydrate ligands on the leukocytes (e.g., the sialyl Lewis$^x$ molecule) and the selectin molecules on the vascular endothelium. This low affinity binding results in the leukocytes "rolling" along the endothelial wall in a manner that permits a more stable, higher affinity binding to develop via the leukocytes' integrin molecules and the ICAM receptors expressed on the surfaces of the endothelial cells. The expression of both P- and E-selectin has been shown to be transient in vitro and is believed to be transient in vivo. This is consistent with evidence that suggests continued expression of these molecules could result in inflammatory disease due to the continued evasiation of leukocytes from vascular to tissue compartments.

However, normal trafficking of leukocytes from the vascular compartment to gingival tissues is clearly required for the prevention of periodontal disease. Anderson et al., *J. Infect. Dis.* 152: 668 (1985); Etzoni et al., *N. Engl. J. Med.* 327: 1789 (1992). Leukocytes from patients with congenital defects in the expression of the leukocyte B2 integrin receptor CD11/CD18 are unable to bind to their respective ICAM receptors on endothelial cells, and the patients typically suffer from severe periodontal disease. Anderson et al., supra. Recently, a congenital leukocyte adhesion deficiency in the expression of the sialyl-lewis X ligand for E-selectin has been described. Etzoni et al., supra. This defect resulted in severe periodontal disease, thereby confirming the requirement for a functional selectin pathway for the prevention of periodontal disease.

Traditional microbiological and immunological approaches to controlling periodontal disease have attempted to eliminate the pathogenic microorganisms or maintain them at very low levels. These efforts have focused on antibiotic treatment and, more recently, the generation of protective immune responses by vaccination against bacterial antigens. In one study non-human primates immunized with formalin-fixed *P. gingivalis* demonstrated significant increases in serum antibody titers to the organism and a significant reduction in alveolar bone destruction. Perrson et al., *Infect. Immun.,* 62:1026–1031 (1994). Even though the vaccine was effective in suppressing or arresting bone loss and lessening attachment loss, the subgingival plaque in immunized animals still harbored very large numbers of *P. gingivalis,* suggesting that protection against tissue destruction may be multifactorial.

In an earlier study, Ebersole et al. (*Infect. Immun.* 59: 3351–3359 (1991)) immunized nonhuman primates with *P. gingivalis* and *Prevotella intermedia*. They showed that active immunization could elicit a systemic immune response against the organisms, and that *P. gingivalis* immunization could significantly inhibit the emergence of the species during subsequent disease progression. Subgingival plaque indices, however, indicated that few changes could be attributed to immunization, and both bleeding on probing and loss of attachment were higher in areas of ligature-induced periodontitis in immunized animals than in placebo-treated controls. In fact, a significant increase in bone density loss was observed in the ligated teeth of immunized animals. Ebersole et al. noted that it is possible that immunization with one or even several microorganisms in a complex ecosystem could exacerbate the destructive events of such a multifactorial disease.

Despite an understanding of the microbial origins of periodontal disease and its temporal progression, means to arrest or even eliminate the disease have eluded investigators. Quite surprisingly, the present invention provides a means to interfere with and modulate the temporal progression of this and other chronic inflammatory diseases associated with gram-negative bacterial infections, and further fulfills other related needs.

SUMMARY OF THE INVENTION

The present invention provides methods and compositions to treat and prevent inflammatory disease states, particularly chronic inflammatory diseases, that are associated with gram-negative bacterial infection. The most prevalent of these diseases are those associated with anaerobic gram-negative organisms, such as periodontal disease, i.e., periodontitis and gingivitis, and ulcers. The invention provides a method for modulating the progression of periodontal disease in a mammal by administering a compound which inhibits the ability of *P. gingivalis* to inhibit the extravasation of leukocytes from the vascular endothelium to gingival tissues.

The compound useful in the present methods can be specific for LPS of the organism or specific to the endothelial cell ligand which binds the LPS molecule, e.g., polyclonal or monoclonal antibody, or can be a composition of compounds which recognize the components of the LPS-ligand interaction and thereby inhibit the immunosuppressive down-regulation of selectin expression. In the treatment or prevention of periodontal disease, typically the compound is administered to the periodontium, by mouthwash, aerosol, paste or salve. The compound or mixture thereof is administered in an amount sufficient to inhibit the ability of *P. gingivalis* lipopolysaccharide to inhibit the extravasation of leukocytes from the vascular endothelium to gingival or other afflicted tissues. In one embodiment the compounds are monoclonal antibodies that bind specifically to *P. gingivalis* lipopolysaccharide, and in another the compound is an enzyme that specifically degrades components of the lipopolysaccharide of *P. gingivalis* or other causative organism as described herein, e.g., *H. pylori*. The compounds useful in the present methods can be targeted to the affected tissues, e.g., periodontium or gingival tissues, by an antibody that binds to P- or E-selectin, where the antibody can be a bifunctional antibody capable of binding to both P-and E-selectin, and in some embodiments the compound is directly linked to the antibody.

In other embodiments the invention provides methods for screening compounds which attenuate the ability of LPS that inhibits the extravasation of leukocytes from the vascular endothelium. The methods comprise contacting cells which are capable of expressing a selectin molecule, such as HUVECs, with LPS from a selected organism, such as *P. gingivalis*, in the presence and absence of the compound being screened for the ability to inhibit LPS-induced inhibition of selectin expression. Expression of selectin is stimulated, e.g., by exposure to *E. coli* LPS, tumor necrosis factor, or interleukin-1, and the expression of selectin in the presence or absence of said compound is measured and the ability of the compound to attenuate or prevent LPS-induced inhibition of selectin expression determined. This method is particularly useful for screening mutants of AOAH which have increased ability to inhibit or degrade the LPS molecule being tested.

The invention also provides a method for diagnosing host susceptibility to chronic inflammatory disease associated with an anaerobic or microaerophilic gram-negative bacterial infection, such as periodontal disease, chronic gastritis or gastroduodenal ulcers. The method comprises contacting cells of said host capable of expressing selecting, such as endothelial cells, with a diagnostic marker specific for the ligand that binds to LPS of the disease-associated bacteria, e.g., *P. gingivalis* or *Helicobacter pylori*. The presence of said ligand is indicative of the susceptibility of the host to LPS-mediated inhibition of selectin expression and thus the chronic inflammatory disease.

Three separate experiments were performed. The mean and inter-assay standard deviation from the mean are shown.

Figure 10:
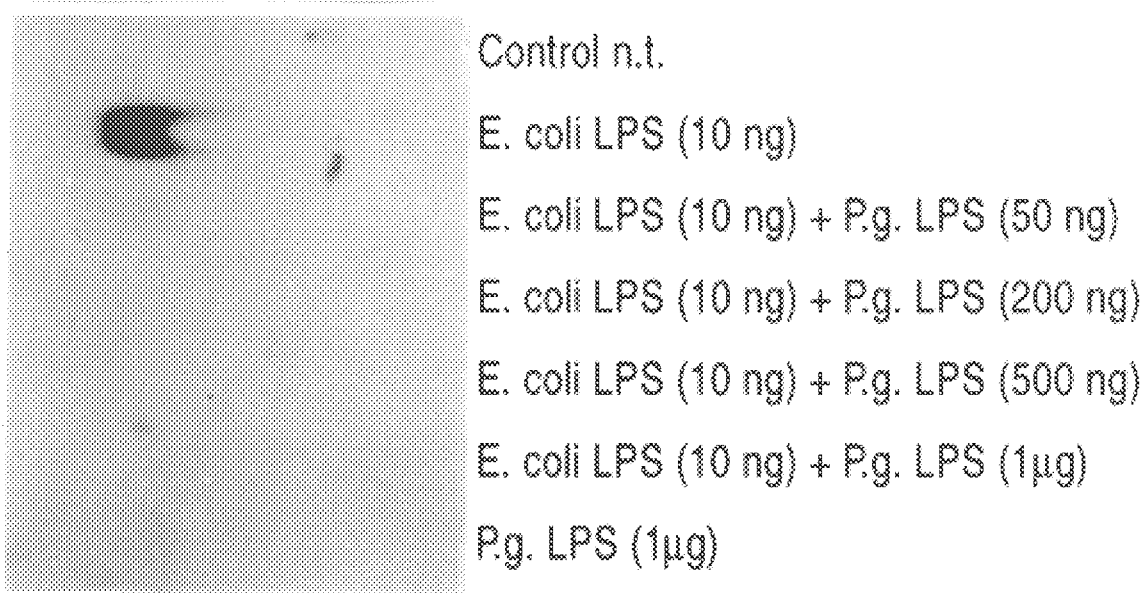

FIG. 10 shows that increasing concentrations of *P. gingivalis* LPS inhibits monocyte chemoattractant protein 1 (MCP-1) RNA expression that is stimulated in human gingival fibroblasts by *E. coli* LPS.

Figure 11:
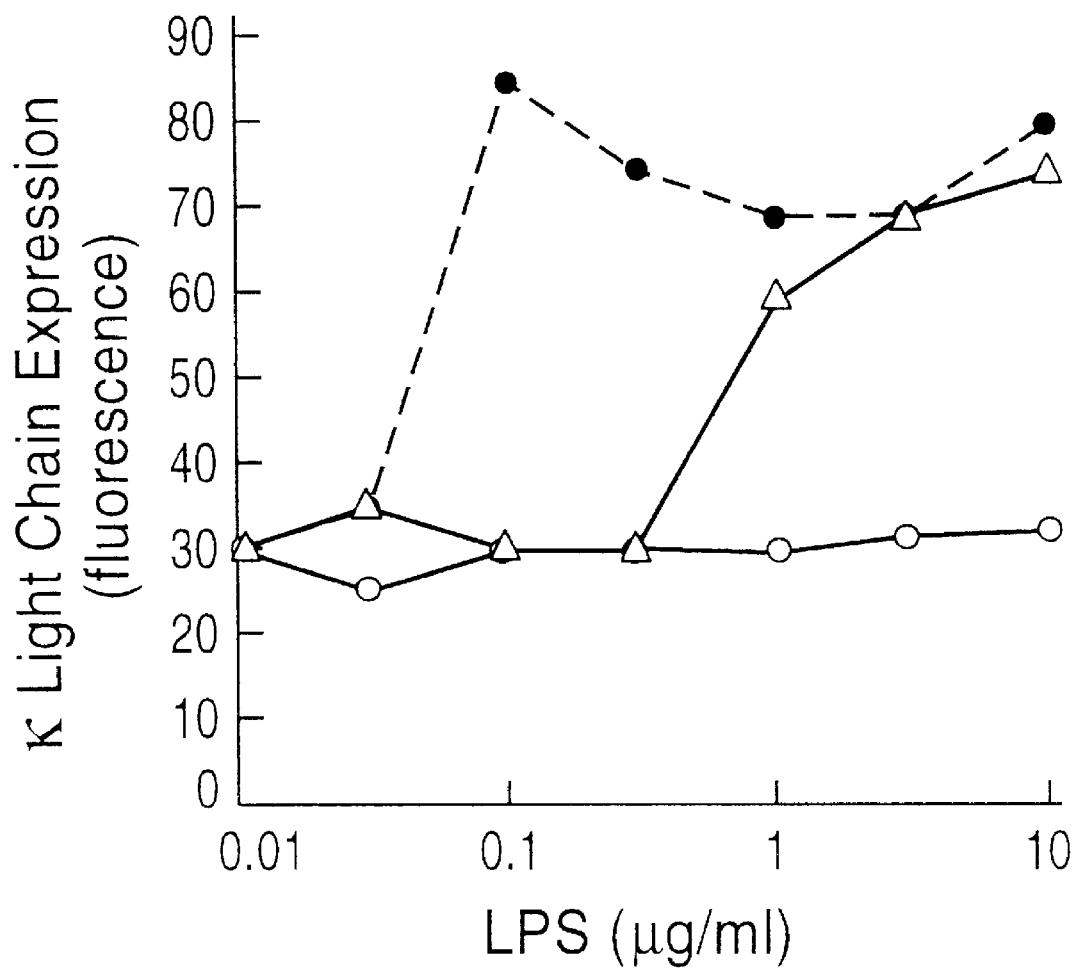

FIG. 11 shows that *E. coli* LPS was able to induce K light chain expression but *P. gingivalis* LPS did not in a murine B lymphoma line, 70 Z/3. *P. gingivalis* LPS was able to inhibit the ability of the *E. coli* LPS to induce K light chain expression.

Figure 12:
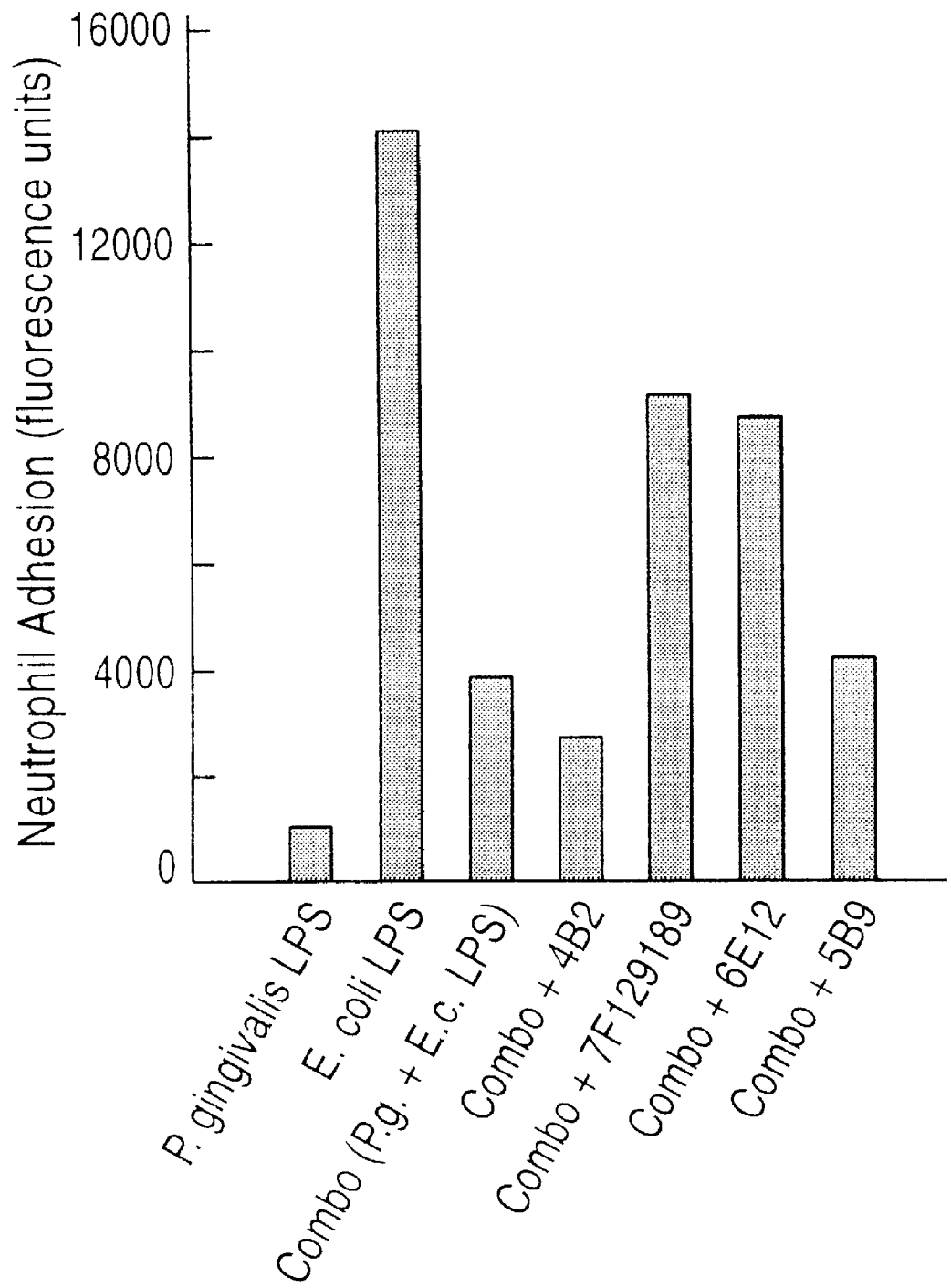

FIG. 12 demonstrates the effect of monoclonal antibody to *P. gingivalis* LPS on *E. coli* induced neutrophil adhesion.

DESCRIPTION OF THE SPECIFIC EMBODIMENTS

The present invention provides methods and compositions to treat and prevent chronic inflammatory disease states that are associated with anaerobic gram-negative bacterial infection. The most prevalent of these diseases are periodontal disease, i.e., periodontitis and gingivitis, and ulcers. As with most gram-negative organisms, the bacteria associated with these diseases have lipopolysaccharide ("LPS") in the outer bacterial membrane. Among members of Enterobacteriaceae LPS is a potent inflammatory mediator and can even lead to endotoxin shock. It has been a paradox that the LPS of gram-negative anaerobes involved in chronic inflammatory diseases are generally less toxic.

As one aspect of the present invention, it has now been discovered that LPS from gram-negative anaerobes can be a potent inhibitor of early aspects of the normal inflammatory process, i.e., the emigration of leukocytes from the vascular endothelium. Inhibition or disruption of the normal inflammatory pathway from the vascular endothelium by the gram-negative anaerobic bacteria represents a potential new mechanism of host invasion.

Although inhibition of leukocyte emigration is not complete, since periodontitis, gingivitis and the like are replete with neutrophils and lymphocytes, the present invention demonstrates that certain bacteria like *P. gingivalis* have adapted a host evasion strategy that involves a form of inflammation masking. By containing a less virulent and immunosuppressive LPS they have changed the very molecule which would normally lead to their detection and elimination by the immune system. The present invention provides methods and compositions for preventing or counteracting the inhibition of the normal immune function by these infections, for restoring immune function at sites of harmful bacterial-induced inflammation, and methods for diagnosing host susceptibility to bacterial-induced inflammatory responses that are potentially destructive of host tissue.

The present invention provides the ability to inhibit the disruption of a normal inflammatory response that is mediated by the LPS of certain gram-negative bacteria, particularly the gram-negative anaerobic bacteria associated with chronic diseases in mammalian hosts, including human hosts. LPS has been shown to inhibit expression of selectin molecules on the surfaces of vascular endothelial cells, thereby impeding the normal flow of leukocytes, particularly neutrophils, to the extravascular tissue and the site of infection. Adequate responses by neutrophils and other leukocytes are essential to preventing or overcoming a bacterial infection. By reversing or preventing the suppression of emigration of these leukocytes through the vascular endothelium according to the present invention, thereby permitting a more "normal" immune response, the gram-negative infections can be more readily treated by conventional therapies, as desired. The genes encoding the selectin cell surface glycoproteins, including E-selectin. (ELAM) and P-selectin (GMP140/PADGEM, have been cloned and sequenced. See, e.g., Bevilacqua et al., Science 243: 1160 (1989) and Johnston et al., Cell 56: 1033 (1989), respectively, which are incorporated herein by reference.

The present invention is directed toward prevention and treatment of a wide variety of infections due to anaerobic gram-negative bacilli that are typically associated with pathological inflammatory diseases. One of the most prevalent of such infections is associated with periodontal disease, particularly gingivitis and periodontitis. These diseases are typically associated with polymicrobial infections, but prominent among the microbiota associated with these diseases are members of the genera Bacteroides (e.g., *B. melaninogenicus*), Porphyromonas (e.g., *P. gingivalis, P. intermedia*), Prevotella (e.g., *P. denticola, P. loescheii*), Eikenella (e.g., *E. corrodens*), and Wolinella (e.g., *W. recta*).

Other pathological inflammatory diseases associated with infections due to microaerophilic gram-negative bacilli and that are susceptible to treatment or prevention according to the present invention include chronic gastritis or gastroduodenal ulcers, which have recently been associated with chronic infection by *Helicobacter pylori*.

In another embodiment the invention concerns the treatment of infections due to organisms of the family Pseudomonadaceae. These gram-negative bacteria typically cause infections in the presence of immunosuppressive conditions in a host, and are extremely difficult to treat with conventional antibiotic therapy. The LPS from these organisms inhibits the expression of selectins by vascular endothelial cells, thereby rendering the bacteria less exposed to normal host defenses. Preventing or attenuating the relative absence of selectin expression according to the present invention permits a more normal and effective host immune response, either separately or in conjunction with other treatment modalities. Clinically normal periodontal tissue has been reported to have elevated levels of expression of E-selectin and the inflammatory chemokine MCP-1. The increased expression of these inflammatory mediators, in close proximity to bacterial plaque, is consistent with a state of low level inflammation in clinically normal tissue. Offered by way of possible explanation but not limitation, the ability of *P. gingivalis* LPS to block direct E-selectin expression in a local environment such as the periodontium may contribute to the colonization of the tooth root surface and result in the bacterial blooms that occur in periodontal disease. In addition, inhibition of the inflammation normally induced by a wide variety of other bacteria may contribute to the characteristically large numbers of different bacteria found in these lesions.

In accordance with the present invention, compounds which can inhibit the interaction of the immunosuppressive LPS with its corresponding ligand on the endothelial cell are effective in permitting a more effective immune response, i.e., the emigration of leukocytes, and particularly neutrophils, to the extravascular tissue where the infecting organisms can be attacked and destroyed. Compounds which are effective inhibitors of the anaerobic or microaerophilic bacterial LPS interaction with the ligands on the endothelial cells are identified in screening assays and the like.

Particularly useful inhibitors of the LPS-ligand interaction, and thus effective mediators of the chronic inflammatory disease process, are antibodies and binding fragments thereof specific for the LPS or the corresponding ligand. Thus, the antibodies or other compounds which are employed in the compositions and treatments of the present invention are those which demonstrate the ability to inhibit or reverse the bacterial LPS-mediated inhibition of selectin expression, e.g., the inhibition of *E. coli* LPS-induced selectin stimulation as demonstrated for *P. gingivalis* LPS in the Examples below.

Thus, the antibodies and binding fragments thereof useful in the present invention can be either polyclonal or monoclonal, but preferably are monoclonal. If polyclonal, they can be in the form of antiserum or monospecific antibodies, such as purified antiserum which has been produced by immunizing animals with *P. gingivalis* or the purified LPS thereof. Preferably, however, the antibodies are monoclonal antibodies so as to minimize the administration of extraneous proteins to an individual. Monoclonal antibodies which bind to the different components of the anaerobic or microaerophilic gram-negative bacterial LPS molecule or the endothelial cell ligands thereof can be prepared according to well known protocols. See. e.g., Skare et al., *J. Biol. Chem.* 268: 16302–16308 (1993), U.S. Pat. Nos. 4,918,163 and 5,057,598, which are incorporated herein by reference.

For administration to humans, e.g., as a component of a composition for in vivo treatment, the monoclonal antibodies are preferably substantially human to minimize immunogenicity, and are in substantially pure form. By "substantially human" is meant that the immunoglobulin portion of the composition generally contains at least about 70% human antibody sequence, preferably at least about 80% human, and most preferably at least about 90–95% or more of a human antibody sequence. When referring to "antibody," it will be understood that non-immunoglobulin sequences may optionally be present in the molecule so long as the molecule retains the ability to bind the LPS or LPS ligand present on the endothelial cell.

As the generation of human monoclonal antibodies to a ligand present on human cells may be difficult with conventional human monoclonal antibody techniques, it may be desirable to transfer antigen binding regions (e.g. the F(ab')$_2$, variable or hypervariable (complementarity determining) regions), of non-human monoclonal antibodies, such as from a murine monoclonal antibody that has been made to ligand purified from cells via an affinity interaction with the LPS, to human constant regions (Fc) or framework regions using recombinant DNA techniques, thereby producing substantially human molecules. Such methods are generally known in the art and are described in, for example, U.S. Pat. No. 4,816,397, EP publications 173,494 and 239,400, which are incorporated herein by reference. Alternatively, one may isolate DNA sequences which code for a human monoclonal antibody or portion thereof that specifically binds to the human ligand, or to anaerobic or microaerophilic bacterial LPS antigen by screening a DNA library from human B cells according to the general protocol outlined by Huse et al., *Science* 246:1275–1281 (1989), and described in WO 90/14430, incorporated herein by reference, and then cloning and amplifying the sequences which encode the antibody (or binding fragment) of the desired specificity. In yet other embodiments, single chain binding polypeptides can be made which bind to the immunosuppressive anaerobic or microaerophilic bacterial LPS or to the corresponding cellular ligand(s) thereof. These single chain polypeptides may be produced by cloning and joining the variable regions of the heavy and light chains of a monoclonal antibody which binds to the LPS antigen or endothelial cell ligand(s) thereof. Methods for the production of single chain binding polypeptides are described in detail in, e.g., U.S. Pat. No. 4,946,778, which is incorporated herein by reference.

Other compounds which are capable of binding to the immunosuppressive anaerobic or microaerophilic bacterial LPS molecule or to the cellular ligand thereof and which inhibit the immunosuppressive effects of the corresponding bacteria, but which are not derived from immunoglobulin molecules, can be isolated according to established protocols. For example, LPS-specific or LPS/ligand-specific binding polypeptides can be isolated by screening vast libraries of random or semi-random polypeptides. The polypeptide libraries can be expressed and isolated as a component of a phage coat protein (e.g., Scott and Smith, *Science* 249: 386 (1990); Dower et al., WO 91/19818), as part of a polyribosome (e.g., Kawasaki, WO 91/05058), or without a ribosome present (Gold et al., WO 93/03172), each of which publications is incorporated by reference herein. Once the binding molecule is identified according to the desired selection procedure, the molecule is tested as described herein for the ability to inhibit the suppression (e.g., by *P. gingivalis*) of the upregulation of selectin expression as can be caused by, e.g., *E. coli* LPS, TNF or IL-1, and thus are useful in treating or preventing the chronic inflammatory process associated with such bacteria. Once the monoclonal antibody, LPS- or ligand-binding polypeptide is identified it can be expressed in large quantities for production purposes.

The methods of the invention can also be used in a screening assay to identify effective compounds. According to one protocol, the compounds are screened for the ability to ameliorate *P. gingivalis* or *H. pylori* LPS-induced inhibition of selectin expression. Cells which are capable of expressing a selectin molecule, e.g., E- or P- selectin, are contacted with the bacterial LPS, e.g., that of *P. gingivalis*, in the presence and absence of the compound being screened for the ability to inhibit *P. gingivalis* LPS-induced inhibition of selectin expression. Selectin expression is stimulated and measured in the presence or absence of the compound being tested. The ability of the compound to inhibit *P. gingivalis* LPS-induced inhibition of selectin expression is then determined. The cells expressing selectin are conveniently human umbilical endothelial cells (HUVECs), and selection expression is preferably induced by *E. coli* LPS, but tumor necrosis factor, interleukin-1 or other stimulators may also be tested.

Compounds which bind the immunosuppressive anaerobic or microaerophilic bacterial LPS molecule or to the cellular ligand thereof and which inhibit the immunosuppressive effects of the corresponding bacteria, such as monoclonal antibodies, are useful in a wide variety of therapeutic and prophylactic settings. These compounds are administered in compositions to prevent and/or treat the chronic inflammatory diseases associated with infections by such bacteria, e.g., periodontitis, gingivitis, chronic gastritis or gastroduodenal ulcers, and the like.

Neutrophils, monocytes and vascular endothelial cells have been shown to contain acyloxyacyl hydrolase ("AOAH"), an enzyme that detoxifies bacterial LPS. The presence of neutrophils that contain AOAH, or the delivery of purified AOAH to the infected tissue, may facilitate a more rapid resolution of the infection. The isolation and purification of AOAH from human neutrophils has been described, e.g., U.S. Pat. No. 5,013,661, incorporated herein by reference, as has the cloning and expression of AOAH molecules and subunits thereof by recombinant DNA techniques, PCT publication WO 92/04444 and U.S. Pat.

No. 5,281,520, incorporated herein by reference. AOAH can be targeted to the sites of chronic bacterial infection via antibodies which bind to selectins, e.g., E-selectin or P-selectin. The targeting antibodies are preferably monoclonal antibodies, and can be linked directly to the AOAH molecule, as a fusion protein, or indirectly, e.g., contained within a liposome preparation targeted by the anti-selectin antibody or binding fragment thereof. The AOAH can be linked to an antibody which has bifunctional specificity, i.e., capable of binding to both E-selectin and P-selectin.

In other instances, the immunosuppressive yet relatively nontoxic LPS prepared from these organisms (e.g., *P. gingivalis*) can also be administered in sufficient quantities to treat or at least ameliorate the endotoxin shock that is often associated with acute infections by gram-negative organisms having more toxic LPS moieties, e.g., *E. coli*, Enterobacter, Salmonella, and the like. The therapeutically administered LPS can be modified to further reduce the toxicity thereof in a patient while retaining the ability to inhibit the stimulation of selectin expression by the LPS of the infecting organism.

The LPS molecules, or mimetics thereof, that inhibit the expression of selectin molecules can also be used as drugs to inhibit other selectin-mediated inflammation, such as that involved in accumulation of lymphocytes in the skin in certain skin diseases, e.g., psoriasis and contact dermatitis, during acute inflammation of the lung (adult respiratory distress syndrome), reperfusion injury, and the like.

As used herein, the terms "treatment" or "treating" include: (1) preventing such disease from occurring in a subject who may be predisposed to these diseases but who has not yet been diagnosed as having them; (2) inhibiting these diseases, i.e., arresting their development; or (3) ameliorating or relieving the symptoms of these diseases, i.e., causing regression of the disease states. For example, with respect to chronic bacterial infections associated with these diseases, treatment according to the present invention will increase the number of neutrophils at the site of infection and thereby increase the phagocytosis or destruction of the infecting bacteria or their toxic components.

The monoclonal antibodies or other compounds useful in the present invention can be incorporated as components of pharmaceutical compositions containing a therapeutic or prophylactic amount of at least one of the monoclonal antibodies or binding fragment thereof with a pharmaceutically effective carrier. For example, monoclonal antibodies or binding fragments thereof to the LPS can be combined with different antibodies which bind to different epitopes on the LPS molecule, or to epitopes on the LPS ligand on the cellular surface, or to other cellular receptors such as E- or P-selectin, to form a treatment "cocktail."

In preparing the pharmaceutical compositions useful in the present methods, a pharmaceutical carrier should be employed which is any compatible, nontoxic substance suitable to deliver the antibodies or binding fragments thereof or therapeutic compounds identified in accordance with the methods disclosed herein to the patient. Sterile water, alcohol, fats, waxes, inert solids and even liposomes may be used as the carrier. Pharmaceutically acceptable adjuvants (buffering agents, dispersing agents) may also be incorporated into the pharmaceutical composition. The antibodies and pharmaceutical compositions thereof are particularly useful for parenteral administration, i.e., intravenously, intraarterially, intramuscularly, or subcutaneously. Local administration can also be effective, particularly in the treatment or prevention of periodontal disease, i.e., periodontitis and gingivitis, where the compound is contained in a mouthwash solution, paste, salve, ointment or gel and is applied directly to the affected tissues. The concentration of compound such as an antibody in a formulation for administration can vary widely, i.e., from less than about 0.5%, usually at least 1% to as much as 15 or 20% or more by weight, and will be selected primarily based on fluid volumes, viscosities, etc., preferred for the particular mode of administration selected. Actual methods for preparing administrable compositions will be known or apparent to those skilled in the art and are described in more detail in, for example, *Remington's Pharmaceutical Science*, 17th Ed., Mack Publishing Co., Easton, Pa. (1985), which is incorporated herein by reference.

The compounds of the invention useful in inhibiting the immunosuppression associated with the LPS of gram-negative anaerobic or microaerophilic bacteria can be administered for prophylactic or therapeutic treatment. In treatments intended for prophylactic applications, the compositions are administered to a patient susceptible to periodontal disease or other chronic bacterial-induced inflammatory disease, such as chronic gastritis or gastroduodenal ulcers, for example. To prevent recurrent disease and the sequelae thereof, the compositions may be administered daily, weekly or other scheduled maintenance therapy. The regimen will also depend on the dosage and effectiveness thereof, the intended use and the patient's general state of health. The treating physician or dentist will select dose levels and pattern of administration, i.e., route and single or multiple administrations.

In therapeutic applications, the compounds of the invention useful in inhibiting the immunosuppression associated with the LPS of gram-negative anaerobic or microaerophilic bacteria are administered to a patient already suffering from periodontitis or gingivitis or other chronic bacterial-induced inflammatory disease, such as chronic gastritis or gastroduodenal ulcers, in an amount sufficient to at least partially arrest the infecting and, hence, inflammatory process. An amount adequate to accomplish this is defined as a "therapeutically effective dose." Amounts effective for this use will depend upon the compound being employed, the route of administration, the severity of the disease and the general state of the patient's health. Determination of an effective amount of a compound of the invention to inhibit the immunosuppressive components of the infecting bacteria can be determined through standard empirical methods which are well known in the art. Reversal of inhibition of selectin stimulation or merely stimulation of selectin expression, emigration of neutrophils and other leukocytes, and thus efficacy of the subject compositions, can be monitored with a variety of well known in vitro diagnostic procedures.

The invention also provides a method for diagnosing host susceptibility to chronic inflammatory disease associated with an anaerobic or microaerophilic gram-negative bacterial infection, such as periodontal disease, chronic gastritis or gastroduodenal ulcers. The method comprises contacting cells of said host capable of expressing selectins, such as endothelial cells, with a diagnostic marker specific for the ligand that binds to LPS of the disease-associated bacteria, e.g., *P. gingivalis* or *Helicobacter Pylori*. The presence of said ligand is indicative of the susceptibility of the host to LPS-mediated inhibition of selectin expression and thus the chronic inflammatory disease.

The following examples are offered by way of illustration of the invention, not by way of limitation.

EXAMPLE I

In this Example the ability of *P. gingivalis*, an important periodontal pathogen, to stimulate expression of E-selectin, a key initial component of the inflammatory pathway, was examined. An understanding into the relationship between these components is necessary to further understand and treat the disease. Quite unexpectedly, P. gingivalis failed to stimulate E-selectin expression.

Initially the ability of whole bacteria to stimulate E-selectin expression on human umbilical cord endothelial cells (HUVEC) was examined. E-selectin expression was stimulated with varying concentrations of E. coli ATCC 29552 and P. gingivalis ATCC 33277. E. coli ATCC 29552, which contains the 0111:B4 serotype LPS, was obtained from the ATCC; P. gingivalis strains were obtained from Dr. Aaron Weinberg of the University of Washington Department of Periodontics, Seattle, Wash.

Figure 1:
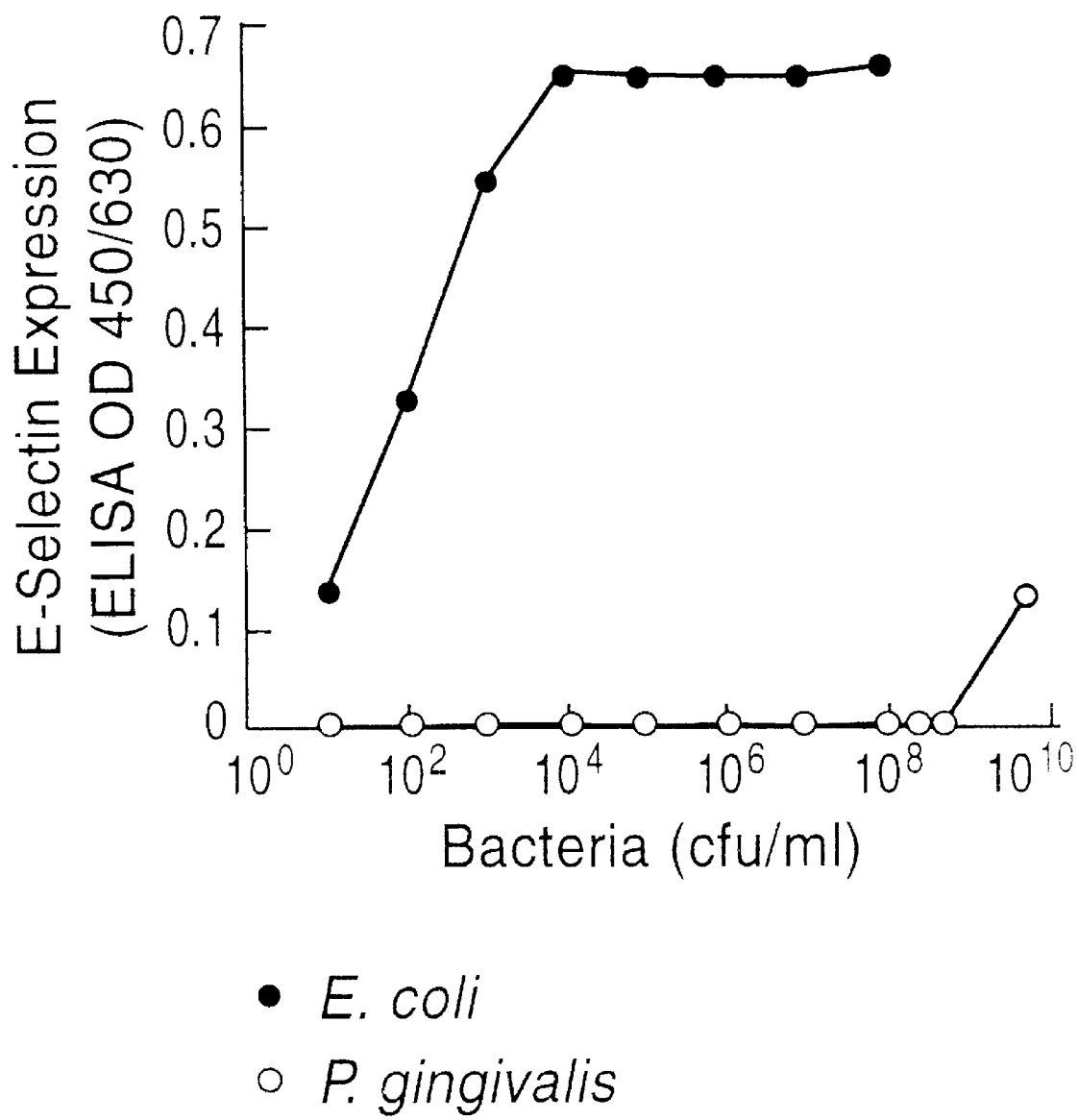
FIG. 1 depicts the stimulation of E-selectin expression with varying concentrations of *E. coli* (ATCC 29552) and the relative absence of E-selectin expression by *P. gingivalis* (ATCC 33277).

Several P. gingivalis strains were examined in addition to ATCC 33277, including 381, A7A1–28, A7436, and 5083. Bacteria were grown on Brucella Blood (Difco) agar supplemented with vitamin K and hemin as described (Nash et al., Manual Clinical Microbiology, chap. 121, 1226 (Amer. Soc. Microbiol.) Wash. D.C. (1991)). Cultures were incubated for 72 hours at 37° C. under either microaerophilic, anaerobic or aerobic conditions as appropriate. Cultures were aseptically suspended in Media 199 supplemented with 4 mM L-glutamine, 90 µg/ml heparin, 1 mM sodium pyruvate, 1 mg/ml human serum albumin, and diluted in the same media to the indicated cell number by calculation from a predetermined conversion factor. Bacterial suspensions were added to a monolayer of fourth passage HUVEC plated in a fibronectin precoated 96 well plate (Costar, flat-bottom) as with the addition of 5% pooled human serum (Gemini Bioproducts). After four hours incubation the plates were washed and assayed for the presence of E-selectin. Each assay was performed in duplicate on three separate occasions. The results of a typical assay are shown in FIG. 1. Endothelial cell viability was determined on duplicate plates after the four hour incubation by the calcein method, as described by the manufacturer (Live/Dead™ Viability/Cytotoxicity Assay, Publ. MP85, Molecular Probes, Inc. 1991).

As shown in FIG. 1, E. coli whole cells were a potent inducer of E-selectin expression. In contrast to E. coli, the addition of P. gingivalis to the endothelial cells did not result in the expression of E-selectin. All strains of P. gingivalis examined failed to stimulate E-selectin expression. Strains examined included the monkey strain (5083) previously used to demonstrate that P. gingivalis can function as a primary pathogen in periodontal disease, as well as a strain (A7436) found to be particularly virulent in a rodent model of infection.

Microscopic examination of the endothelial cell layer after bacterial stimulation revealed no change in endothelial cell shape or loss in cell number. A more quantitative estimate of endothelial cell viability was determined by measuring the hydrolysis of calcein-AM. This reagent detects hydrolysis mediated by an esterase present in eukaryotic but not bacterial cells. The lack of E-selectin expression could not be attributed to endothelial cell toxicity since even high concentrations of these bacteria were not toxic as assayed by these parameters.

These results demonstrated that P. gingivalis was unable to stimulate E-selectin even though this organism has been clearly associated with the inflammatory lesions found in periodontal diseases.

EXAMPLE II

Similar to Example I, this Example examines the comparative abilities of P. gingivalis, E. coli, S. typhimurium, P. aeruginosa, and H. pylori to stimulate expression of E-selectin.

HUVECs (Clonetics, San Diego, Calif.) were maintained in HUVEC growth media Media-199 (Gibco, Gaithersberg, Md.) containing 4 mM L-glutamine, 90 µg/ml heparin, 1 mM Na pyruvate, 30 µg/ml endothelial cell growth stimulant (Biomedical Products, Bedford, Mass.) and 20% fetal bovine serum (Hyclone Lab, Logan, Utah). Cells were used at the fourth passage. Initial experiments conducted on cells in the second or third passage showed no apparent difference in the E-selectin response. HUVEC ($1.4 \times 10^4$/well) were plated in a fibronectin precoated 96 well flat-bottom plate (Costar, Pleasonton, Calif.) in M-199 growth medium the day before stimulation by bacterial cells or bacterial cell products.

Bacteria used included E. coli ATCC 29552, JM 83, MC 1061, and MC 4100 (Dr. J. Somerville, Bristol-Myers Squibb), P. gingivalis strains ATCC 33277, strain 381 A7A1–28, A7436, and 5083, P. aeruginosa strain ATCC 27313, a Bacteroides forsythis strain, and H. pylori ATCC 43504.

For the human E-selectin expression assay, on the day of the assay, bacterial cultures were suspended (from plate grown cells) in M-199 stimulation medium (Media-199 containing 4 mM L-glutamine, 90 µg/ml heparin, 1 mM Na pyruvate, 1 mg/ml human serum albumin, and 5% pooled normal human serum (Gemini Bioproducts, Calabasas, Calif.)) and diluted in the same media to the desired cell number by calculation from a predetermined conversion factor. Conversion factors for each bacterial strain were determined by plate count analysis performed in triplicate by standard procedures for bacterial enumeration. HUVEC were washed with M-199 stimulation without serum, bacterial preparations were then added to the HUVEC monolayer and incubated for four hours at 37° C. under 5% $CO_2$. After the stimulation interval, media was removed, the cells were washed twice in cold PBS, fixed with 0.5% glutaraldehyde (in cold PBS) and placed at 4° C. for 10 minutes. Cells were washed four times with PBS containing 3% pooled goat serum (Sigma, St. Louis, Mo.) and 0.02M EDTA (blocking buffer). After the last wash 0.2–0.3 ml of blocking buffer was added to each well and the plates were stored overnight at 4° C. (this blocking step was complete after one hour, but for convenience overnight incubations were routinely employed). Blocking buffer was removed and 0.1 ml of anti-E-selectin monoclonal antibody (R and D Systems, Minneapolis, Minn.) at 0.25 µg/ml in blocking buffer was added to each well and the plate was incubated at 37° C. for 1 hour. Plates were washed four times in blocking buffer and 0.1 ml of F(ab')$_2$ goat anti-mouse 1 gG specific HRP conjugated second step antibody (Jackson Immunoresearch Labs, West Grove, Pa.) diluted in blocking buffer was added to each well. Plates were incubated at 37° C. for 1 hour, washed four times with blocking buffer, and 0.1 ml of chromogen reagent (TMB in substrate buffer, Genetic Systems, Redmond, Wash.) was added. The reaction was stopped with 0.1 mL of 1N $H_2SO_4$ per well and the plates read in an ELISA reader (BioTek Instruments, Winooski, Vt.) at 450/630 nm. Endothelial cell viability was determined on duplicate plates after the four hour incubation by the calcein-AM method.

Figure 2:
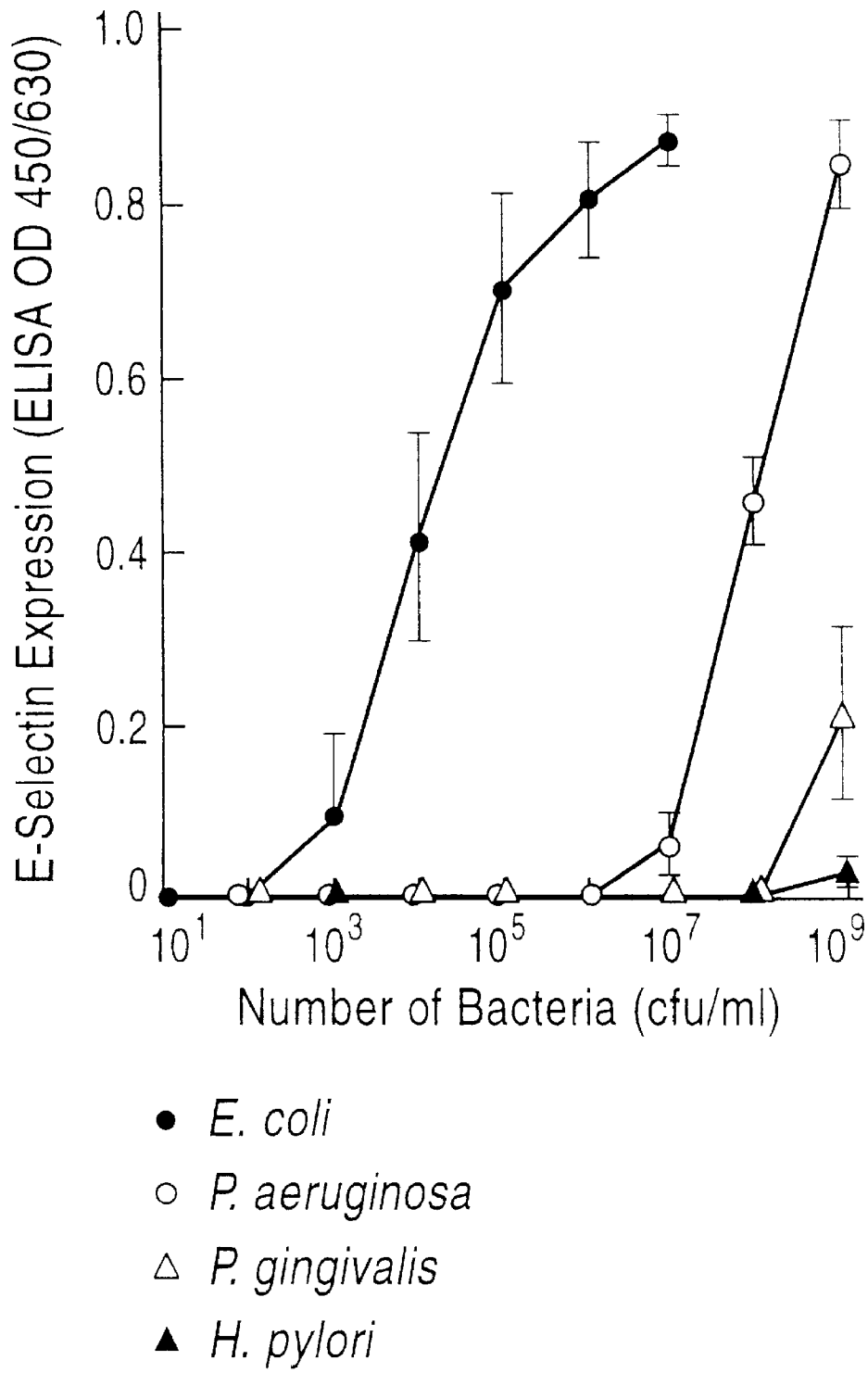
FIG. 2 illustrates the results of E-selectin expression using whole bacteria; *E. coli* ATCC 29552, *P. gingivalis* ATCC 33277, and *H. pylori* ATCC 43504 were examined in five separate experiments. *P. aeruginosa* ATCC 27313 was examined in two separate experiments. The mean and inter-assay standard deviation from the mean are shown.

The results for the ability of whole bacteria to stimulate E-selectin expression on HUVEC are shown in FIG. 2. E. coli cells were a potent inducer of E-selectin expression. H. pylori and P. gingivalis were very poor stimulators of E-selectin expression. At the highest concentrations of bacteria added to the assay, only low levels of E-selectin were observed. Similar to E. coli, P. aeruginosa induced nearly maximal levels of E-selectin expression in the assay, however, approximately three more logs of bacteria were required. The degree of E-selectin stimulation was consistent among different species in a single genus. For example, several different strains of *E. coli* ATCC 25922 and *S. typhimurium* (Table 1) displayed similar dose response curves as shown for *E. coli* ATCC 29552. Five different strains of *P. gingivalis* were examined and failed to stimulate E-selectin expression. Strains examined, but not shown in FIG. 2, included a monkey strain (5083) used to demonstrate that *P. gingivalis* can function as a primary pathogen in periodontal disease, a strain (A7436) that is particularly virulent in a rodent model of infection, and two other strains designated A7A1–28 and 381. Two different strains of *P. aeruginosa* yielded a similar dose response curve (FIG. 2 and Table 1). Microscopic examination of the endothelial cell layer after bacterial stimulation revealed no change in endothelial cell shape or loss in cell number at the bacterial concentrations employed in the assay.

TABLE 1

E-selectin stimulation: Effect of different strains of bacteria*

| Bacteria (cfu) | *E. coli* (ATCC 25922) | *E. coli* (JM83) | *S. typhimurium* (A568) | *P. aeruginosa* (ATCC 27316) |
|---|---|---|---|---|
| $10^9$ | ND | ND | ND | .84 ± .01 |
| $10^8$ | ND | ND | ND | .36 .05 |
| $10^7$ | ND | ND | ND | .07 .05 |
| $10^6$ | .71 .20 | .83 .07 | .66 .14 | 0 |
| $10^5$ | .71 .06 | .74 .05 | .44 .22 | 0 |
| $10^4$ | .52 .08 | .38 .11 | .21 .04 | 0 |
| $10^3$ | .20 .10 | .19 .06 | ND | |
| $10^2$ | .03 .04 | ND | ND | |

*Values represent the mean and standard deviation from at least three separate experiments for each strain examined. *E. coli* ATCC 25922 is a clinical isolate whereas *E. coli* JM83 is a laboratory strain. Other laboratory strains (MC1061 and MC4100) yielded similar results in two separate experiments.

A more quantitative estimate of endothelial cell viability was determined by measuring the hydrolysis of calcein-AM. This reagent detects hydrolysis mediated by an esterase present in eukaryotic but not bacterial cells. Poor E-selectin stimulation by *H. pylori* and *P. gingivalis* could not be attributed to endothelial cell toxicity since even high concentrations of these bacteria were not toxic as assayed by these parameters. IL-1 was added as an additional control of the ability of endothelial cells to express E-selectin in the presence of bacteria. At IL-1 concentrations ranging from 0.03 to 20 ng/ml, 10% *P. gingivalis* whole cells did not affect the ability of the endothelial cell monolayer to express E-selectin. In contrast, calcein-AM hydrolysis assays revealed that concentrations of *E. coli* of 108 cfu/ml and greater were toxic.

Figure 3:
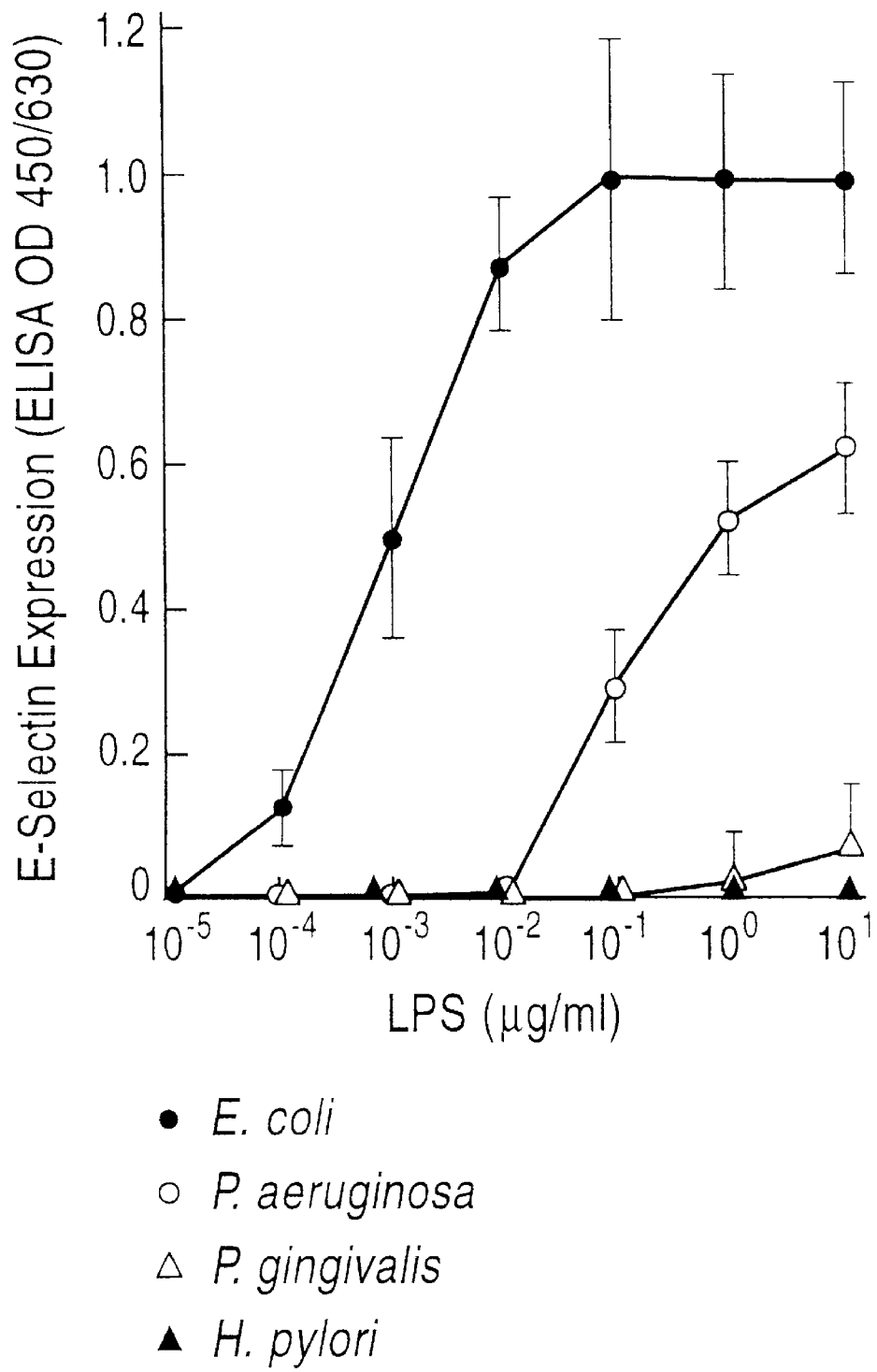
FIG. 3 shows the stimulation of E-selectin expression with LPS preparations. Each assay was performed on at least four separate occasions. The mean and inter-assay standard deviation from the mean are shown.
Figure 4:
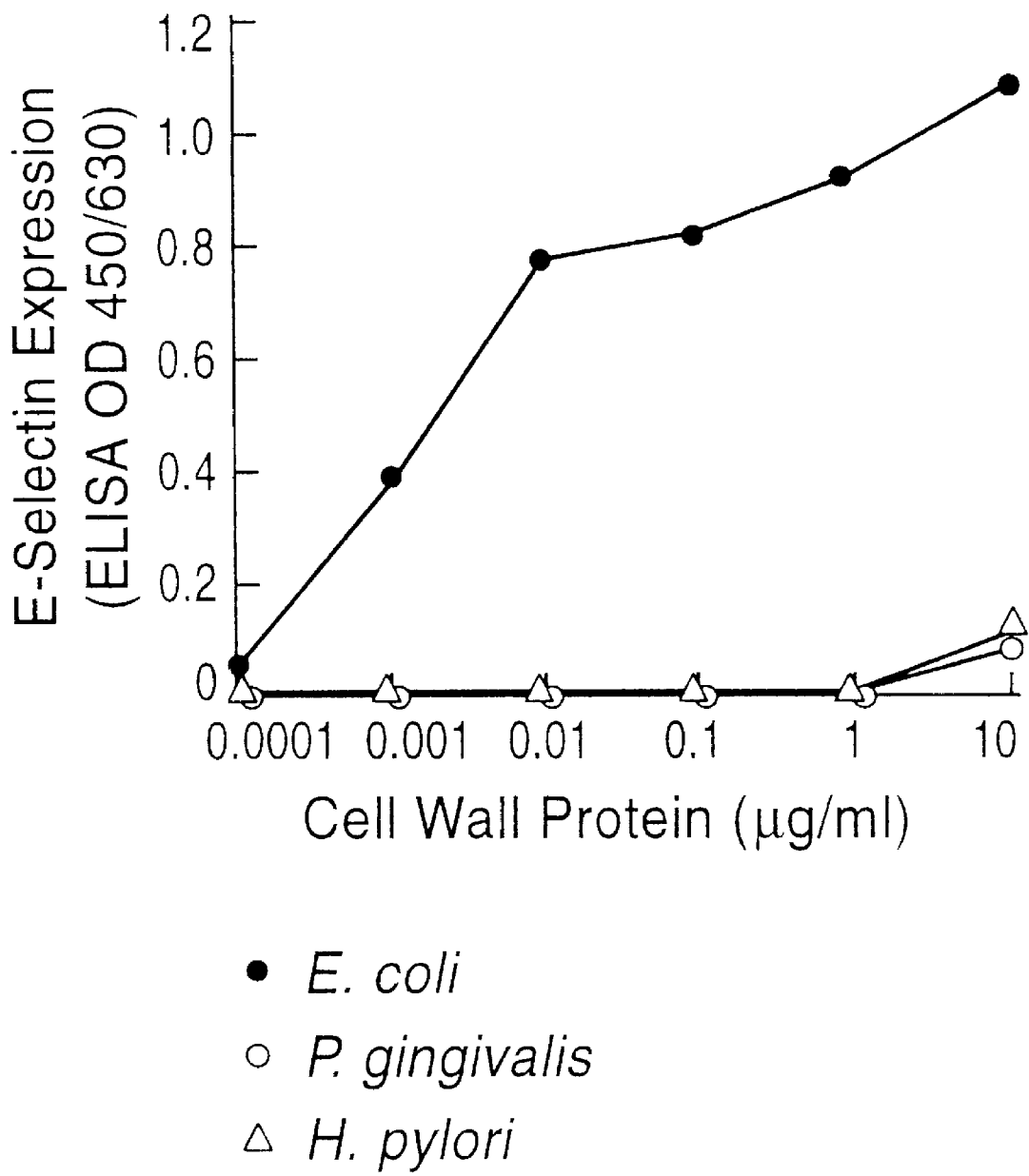
FIG. 4 shows the stimulation of E-selectin expression with bacterial cell wall preparations. Each experiment was performed on at least three separate occasions with similar results. The data are presented as the average of a typical experiment performed in triplicate.

The potential of isolated LPS preparations to directly stimulate E-selectin expression was also examined. Similar experiments are also described in detail in Example III below. As shown in FIG. 3, serum was required to obtain a significant E-selectin response to *E. coli* LPS. The response to *E. coli* LPS was potent, with as little as 1 ng yielding significant expression. In contrast, but similar to the data obtained with whole cells, LPS obtained from *P. gingivalis* and *H. pylori* did not induce E-selectin expression. Also, similar to what was observed with whole cells, *P. aeruginosa* required significantly more LPS to obtain an equivalent *E. coli* level of E-selectin expression. In addition to the data presented in FIG. 3, LPS obtained from three additional strains of *P. gingivalis* (A7A1–28, A7436 and 5083) and LPS obtained from *B. forsythus* also failed to stimulate E-selectin expression (a minimum of three separate experiments at 1 ng/ml was performed with each LPS). No stimulation of E-selectin was observed when these LPS preparations were examined with or without the addition of human serum. Cell walls obtained from *P. aeruginosa* ATCC 27316 yielded a similar significantly reduced response. Cell walls obtained from *H. pylori* ATCC 43504 or *P. gingivalis* ATCC 33277 also were unable to elicit E-selectin expression (FIG. 4). Calcein-AM hydrolysis assays confirmed that these preparations were not toxic to the endothelial cells during the assay.

EXAMPLE III

The ability of *P. gingivalis* LPS to stimulate E-selectin expression was examined in this series of experiments. In addition, the effect of LPS obtained from a related organism, *Bacteroides forsythias*, also believed to be associated with adult periodontal disease was examined.

The effect of various LPS preparations on E-selectin expression was determined by adding LPS preparations to HUVEC monolayers at concentrations of 0.0001, 0.001, 0.01, 0.1 and 1.0 µg/ml, as described in Example I above. LPS from *E. coli* was obtained from Sigma (0111:B4); LPS was purified from *P. gingivalis* 33277 and A7A1–28 by the phenol water method of Westphal and Jann, in Methods in Carbohydrate Chemistry 5: 83–91, R. L. Whistler, ed., Academic Press, Inc., New York; LPS was purified from *B. forsythias* and *P. gingivalis* strain 5083 by the cold Mg/ETOH procedure (Darveau and Hancock, *J. Bacteriol.* 155: 831–838 (1983)). All LPS preparations were suspended in $dH_2O$. LPS preparations were determined to be free from contaminating nucleic acid and protein and subjected to gas chromatographic analysis for sugar and fatty acid composition. The composition of the LPS preparations was consistent with previously reported characterizations. Each assay was performed on three separate occasions in duplicate.

Figure 5:
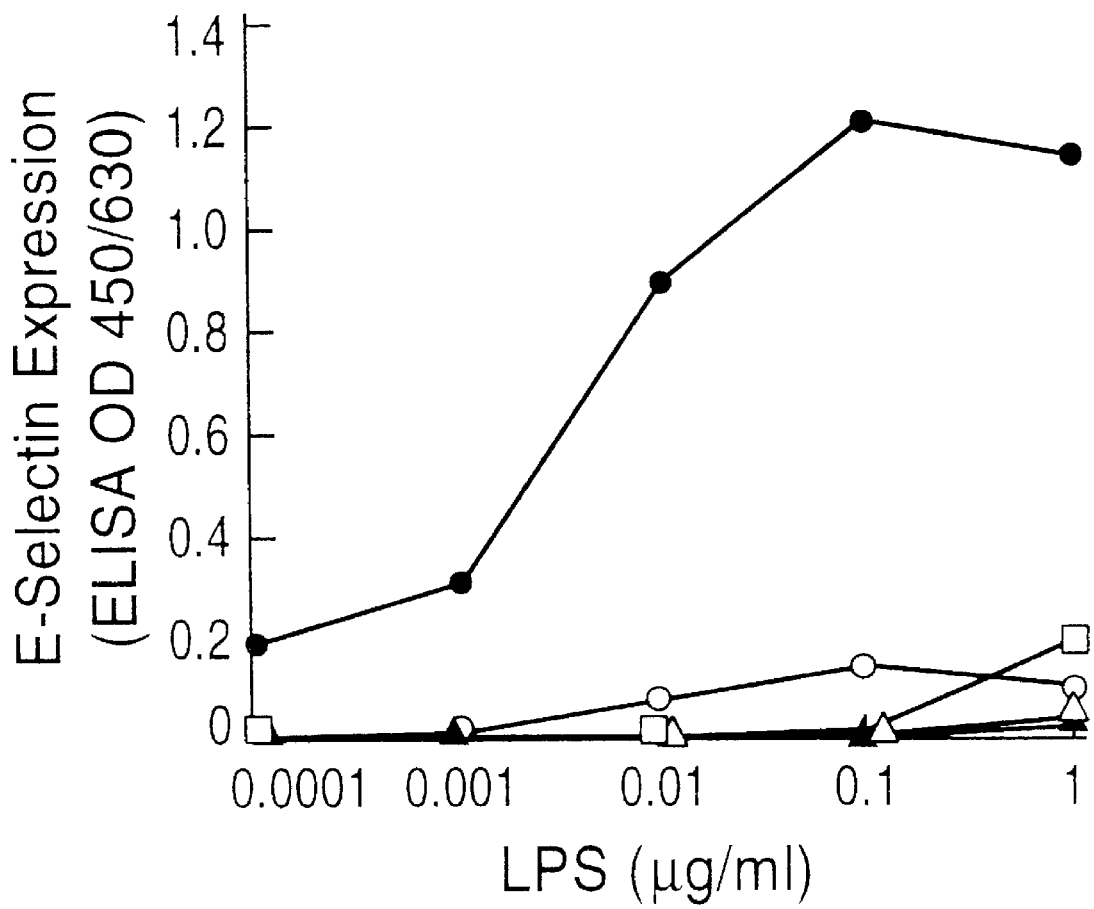
FIG. 5 depicts the effects of LPS preparations from *E. coli*, various strains of *P. gingivalis*, and *B. forsythus* on E-selectin expression by human umbilical vascular endothelial cells.

The results from typical assays are depicted in FIG. 5. No stimulation of E-selectin was observed with these LPS preparations at concentrations 1000 fold greater than that needed to obtain a significant signal from *E. coli* LPS.

As the presence of serum has been shown to be necessary for LPS induced E-selectin expression (Frey et al., *J. Exp. Med.* 176:1665 (1992); Pugin et al., *Proc. Natl. Acad. Sci. USA* 90: 2744 (1993)), the possibility that serum may have interfered with the presentation of the LPS to the endothelial cell was examined. E-selectin stimulations were conducted in the absence of human serum and with serum which had been heat inactivated at 56° C. for 30 minutes. In the absence of serum or in heat-inactivated serum, 10,000 fold more *E. coli* LPS was needed to obtain a significant E-selectin response when compared to stimulation with NHS. Once again, however, no E-selectin response to *P. gingivalis* LPS was observed.

EXAMPLE IV

Having demonstrated that LPS from *P. gingivalis* was unable to stimulate E-selectin upregulation, the ability of *P. gingivalis* LPS to block the upregulation of E-selectin that had been stimulated with either *E. coli* LPS or TNF was also determined.

Figure 6A:
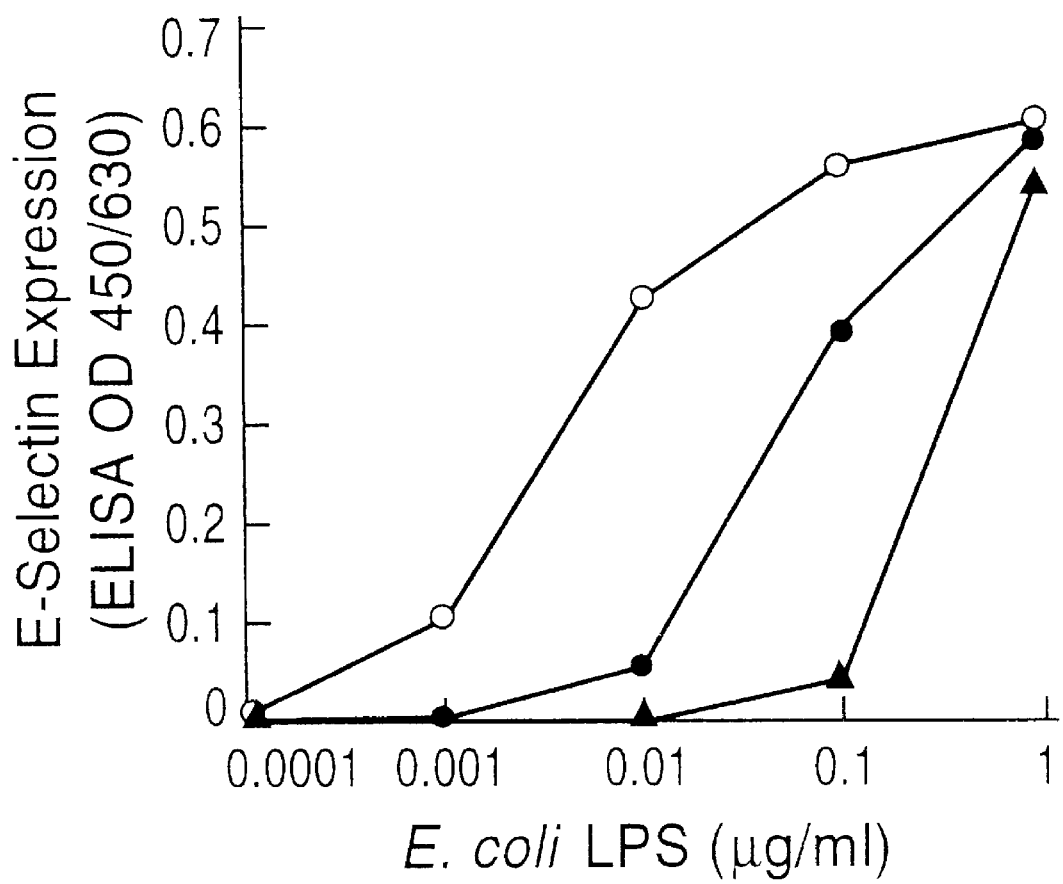
FIG. 6A shows the ability of *P. gingivalis* LPS preparations to inhibit E-selectin expression induced by varying concentrations of *E. coli* LPS.
Figure 6B:
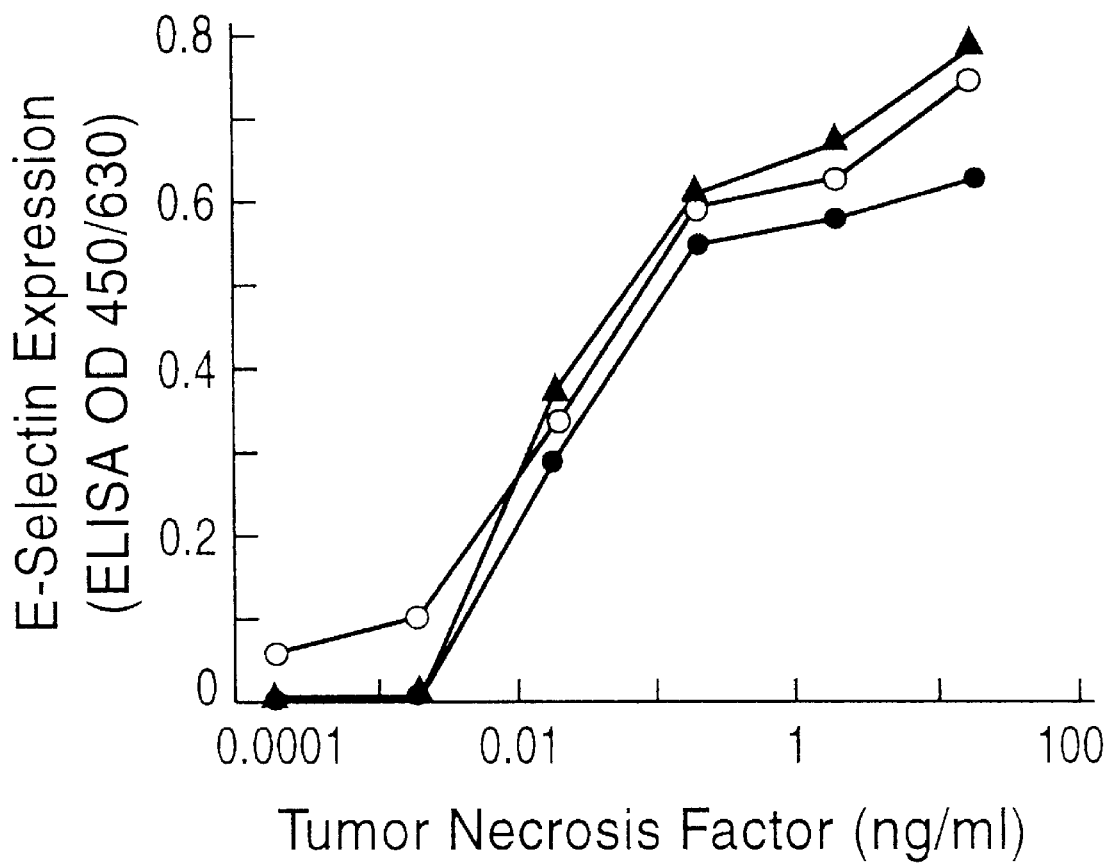
FIG. 6B shows the effect of *P. gingivalis* LPS on E-selectin expression that is induced by tumor necrosis factor (TNF).

Preparations of LPS from *E. coli* and *P. gingivalis* were mixed and then added to endothelial cells. *P. gingivalis* LPS, obtained from strain ATCC 33277 as described in Example III, was mixed at varying ratios with two preparations of *E. coli* LPS or TNF as indicated in FIG. 6A or FIG. 6B, respectively, prior to addition to endothelial cells. Assay of E-selectin was performed as described in Example I. Three separate experiments were performed with similar results. The result of a typical experiment are depicted.

As shown in FIG. 6A, ratios of *P. gingivalis* LPS that were 10 to 100 fold higher than the *E. coli* LPS were able to significantly block the stimulation of E-selectin. As shown in FIG. 6B, when similar mixing experiments were performed with *P. gingivalis* LPS and tumor necrosis factor, no inhibition of E-selectin expression was observed.

Studies were then performed in an effort to determine which portion of the *P. gingivalis* LPS was responsible for the ability to selectively inhibit E-selectin expression. *P. gingivalis* LPS was selectively degraded into its lipid A and polysaccharide components (LPS-PS) by hydrolysis in the presence of 1% acetic acid for 30 min. Fractions were separated by centrifugation and analyzed for their lipid and carbohydrate content by gas chromatography. The composition of each preparation was consistent with previously reported data. *E. coli* LPS (long/ml) was added to an endothelial cell monolayer as described in FIG. 1 (control); the same amount of *E. coli* LPS was mixed with 10 µg/ml of either *P. gingivalis* LPS, LPS-PS, or Lipid-A and analyzed for E-selectin expression.

Figure 7:
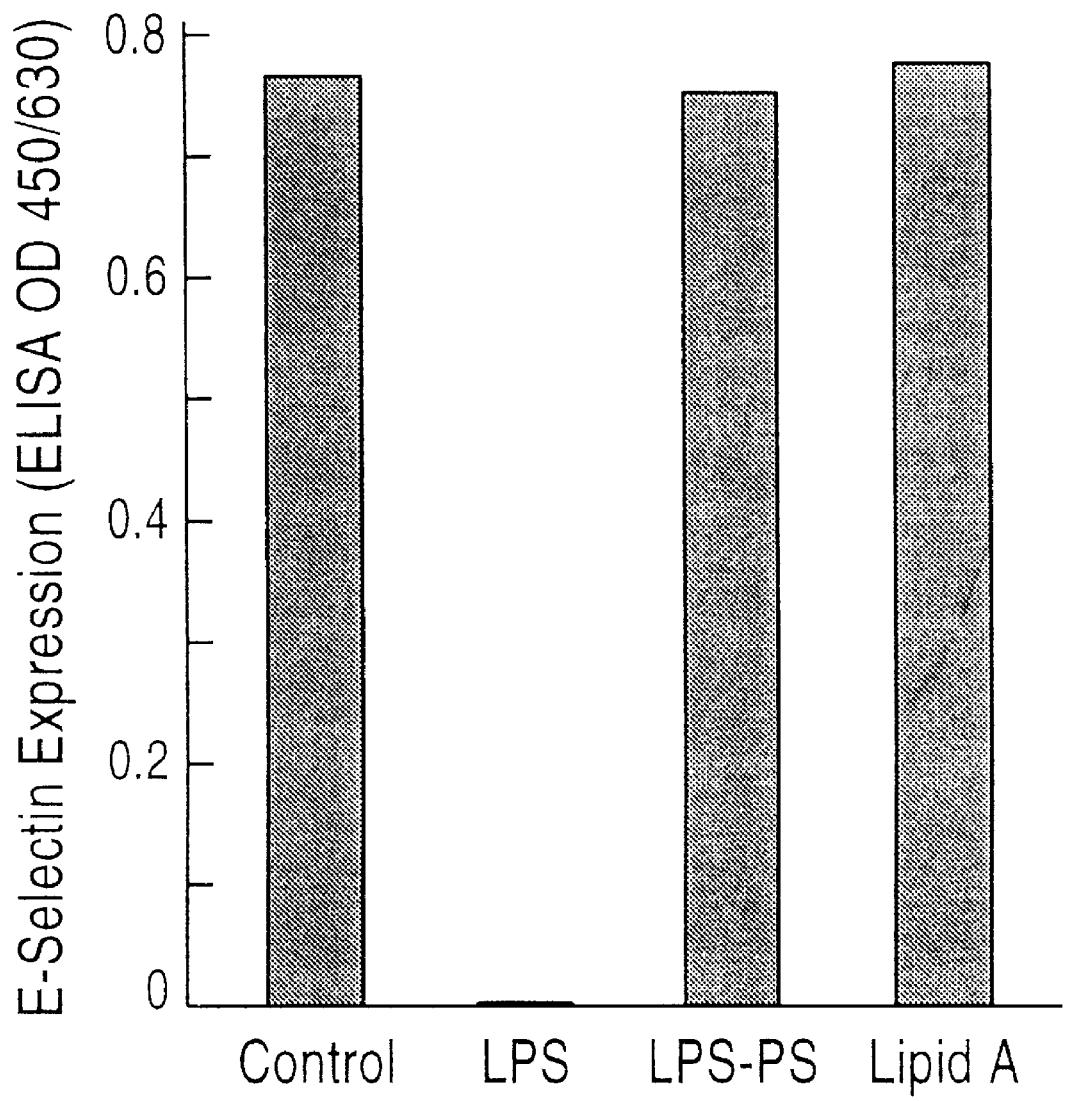
FIG. 7 illustrates the inhibition of E selectin expression induced by *E. coli* LPS by the LPS of *P. gingivalis* compared to a relative lack of inhibition by the lipid A or polysaccharide ("LPS-PS") fractions of *P. gingivalis* LPS.

FIG. 7 shows the results of the E-selectin expression inhibition studies by the *P. gingivalis* LPS fractions. In three separate experiment neither isolated lipid A nor the polysaccharide component when added at 10 µg/ml were able to block E-selectin activation by 10 ng/ml *E. coli* LPS. The inability of these fractions to block when added at 100 fold excess suggests that both components of the LPS molecule may be required for inhibition of E-selectin expression. However, selective degradation of a key LPS component due to the hydrolysis procedure was not ruled out.

*P. gingivalis* LPS also blocked E-selectin expression by *Actinobacillus actinomycetemcomitans* and *Salmonella typhimurium* LPS.

In other experiments *P. gingivalis* LPS was shown to block E-selectin expression stimulated by cell walls obtained from *Leptotrichia buccalis* (ATCC 14201), *E. coli* ATCC 29552, *Haemophilus parainfluenzae* (BMS C128), *Neisseria flavescens* (ATCC 13120), *Eikenella corrodens* (ATCC 23834), and *Fusobacterium nucleatum* (ATCC 25586).

EXAMPLE V

Antibodies that bind to *P. gingivalis* were examined for the ability to prevent or reverse the inhibition of E-selectin expression that is mediated by *P. gingivalis* LPS.

Figure 8:
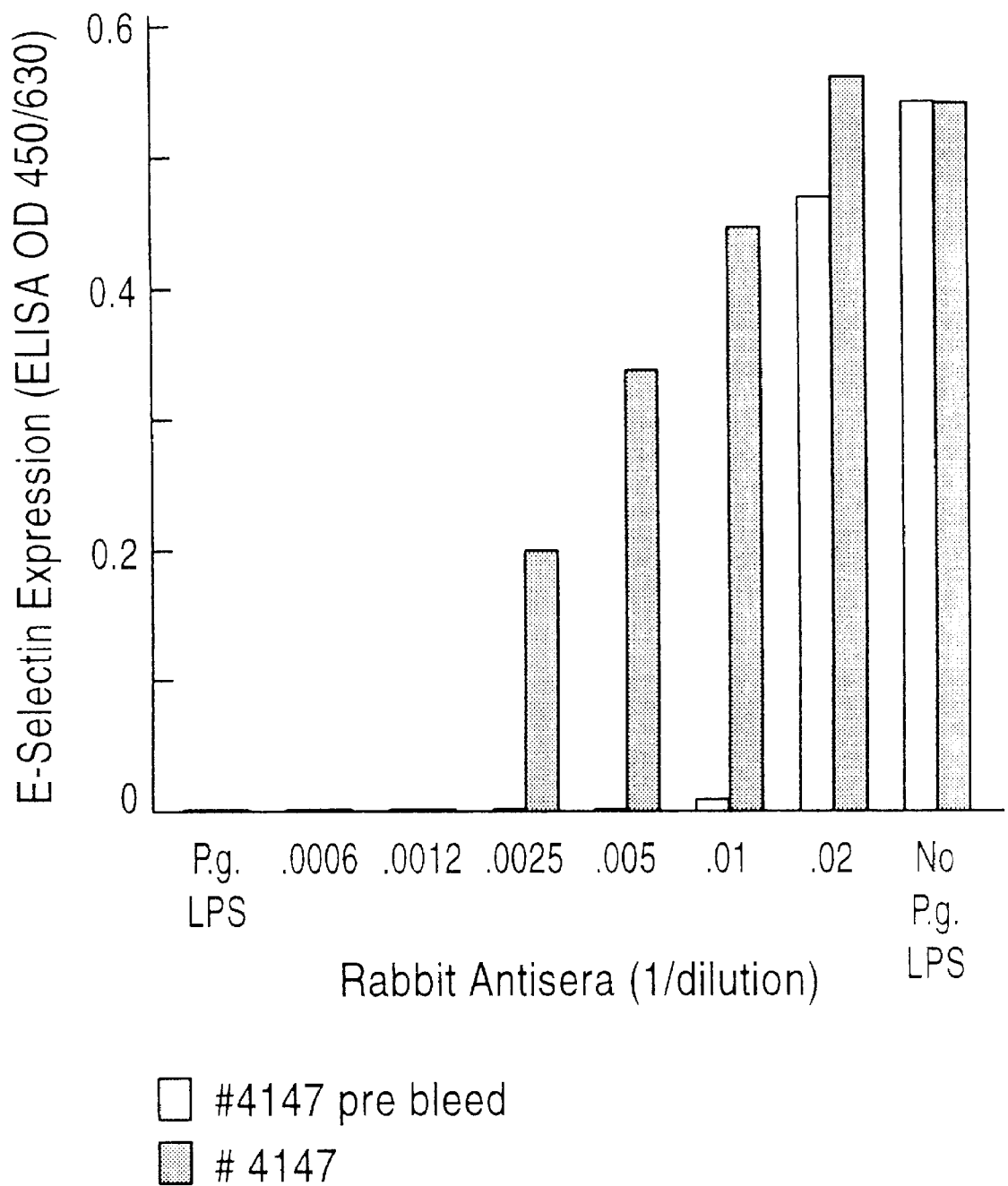
FIG. 8 demonstrates the ability of various dilution of rabbit antisera prepared against *P. gingivalis* to block the ability of *P. gingivalis* (ATCC 33277) LPS to inhibit *E. coli* LPS-mediated upregulation of E-selectin on HUVECs.

Endothelial cells were stimulated with 10 ng/ml of *E. coli* LPS. As shown in FIG. 8, last column, there was an E-selectin response when no *P. gingivalis* LPS was mixed with the *E. coli* LPS prior to addition to the endothelial cells. If however, 0.5 µg/ml *P. gingivalis* LPS was pre-mixed with the *E. coli* LPS prior to addition to the endothelial cells, there was a complete inhibition of the E-selection response, as shown in the first column of FIG. 8 labeled "P.g. LPS".

Varying dilutions of pre-immune and immune rabbit sera (immunized with whole *P. gingivalis*) were then preincubated with the *E. coli* and *P. gingivalis* LPS preparations. Preimmune and immune rabbit sera were diluted 1/12.5, then serially for several two-fold dilutions in "Endochow" (M-199, GIBCO with 4 mM L-glutamine, 90 µg/ml heparin, 1 mM sodium pyruvate) without serum or endothelial cell growth factors. The diluted sera was combined 1:1 with *P. gingivalis* LPS (concentration at 1 µg/ml) in the same media and the mixture left at room temp. for about 1 hr. 100 µl of the rabbit sera/*P. gingivalis* LPS mixture was then mixed with 100 µl of *E. coli* 0111:B4 LPS (final concentration of 10 ng/ml). 100 µl of this mixture was then added to HUVECs (previously washed 1× with media, without serum) to stimulate E-selectin expression at 37° C. under 5% $CO_2$ for 4 h. After stimulation the media was removed from the plates and the cells washed 2× in cold PBS (100 µl per well). 100 µl of 0.5% glutaraldehyde (in cold PBS) was added per well and plates cooled to 4° C. for 10 minutes. Plates were then washed 4× using PBS with 3% normal goat serum and 0.02M EDTA (200300 µl per. well). After the last wash, 200–300 PBS/goat serum/EDTA was added per well and the plates stored overnight at 4° C. All antibodies were diluted in PBS/goat serum/EDTA described above. The blocking reagent was then removed from the wells and 100 µl of primary antibody added (usually a mouse anti-ELAM monoclonal, at 0.25 µg/ml). Plates were incubated at 37° C. for 1 hr and then washed 4× in PBS/goat serum/EDTA (200–300 µl per well), and 100 µl/well of second step antibody (Jackson Labs F(ab')$_2$ goat anti-mouse IgG, Fc specific, HRP conjugated [#115-036-071]) was then added. Plates were incubated at 37° C. for 1 hr, washed 4× with PBS/goat serum/EDTA, and received 100 µl of chromogen reagent per well (TMB diluted in substrate buffer). After color development for about 20 min. the reaction was stopped with 100 µl of 1N $H_2SO_4$ per well and the plates were read at 450/630 nm.

As shown in FIG. 8, as the concentration of anti-*P. gingivalis* sera increased there was an increase in the E-selection signal compared to pre-immune sera. This indicated that the anti-*P. gingivalis* antibodies could inhibit the ability of *P. gingivalis* LPS to block *E. coli* LPS mediated E-selectin expression.

EXAMPLE VI

*P. gingivalis* and *H. pylori* Do Not Promote Neutrophil Adhesion to Endothelial Cells This Example demonstrates that in contrast to *E. coli*, *P. gingivalis* does not induce human endothelial cells to be adhesive to neutrophils. The Example also demonstrates that *P. aeruginosa* was a very poor inducer of neutrophil adhesion, and *H. pylori* LPS did not induce neutrophil adhesion to endothelium.

For human neutrophil preparation, blood was obtained from normal healthy human volunteers by venipuncture using heparin containing syringes. Neutrophils were isolated using density gradient centrifugation with Polymorphprep™ (Nycomed Pharma AS, Oslo, Norway) as described by the manufacturer. Contaminating red blood cells were lysed as described in Magnuson et al., *J. Immunol.* 143: 3025–3030 (1989), which is incorporated herein by reference. A portion of the neutrophil preparation was stained, checked for purity, and the remaining cells were suspended to $4 \times 10^6$ cells/ml for fluorescent labeling. Neutrophils were labeled with BCECF-AM (Molecular Probes, Inc., Eugene, Oreg.) according to manufacturer's instructions. Specifically, neutrophils were incubated with 10 mM BCECF-AM in DMSO for 15 min. in the dark, an equal volume of RPMI containing 5% FBS was added and the cells were centrifuged. Neutrophils were washed in PBS and then suspended at $2 \times 10^6$ cells/ml in RPMI containing 1% FCS and kept in the dark.

For the neutrophil adhesion assay the basic procedure described by Magnuson et al., supra, was followed. HUVEC monolayers were prepared as described above for the E-selectin expression assay except that $4 \times 10^4$ HUVEC/well were added to a 96 well plate. HUVEC monolayers were stimulated for 4 hrs with LPS or cell wall preparations as described above for the E-selectin expression assay. After the 4 hr stimulation the HUVEC monolayers were washed with PBS containing 5% FCS and labeled neutrophils were added (0.1 ml of the stock solution, representing about $2\times10^5$ cells/well). The neutrophil/HUVEC cell preparation was covered with foil and placed on a shaker with mild agitation for 30 min at ambient temperature. After 30 min the nonadherent neutrophils were removed by careful aspiration, followed by two washes with PBS containing 5% FCS. After washing, 0.1 ml of a solution containing 50 mM Tris pH 8 and 1% SDS was added to the HUVEC monolayers and the plate was read on a Fluorescence Concentration Analyzer (Baxter Scientific Products, Philadelphia, Pa.) with excitation at 485 nm and emission at 535 nm. The percent of total neutrophils which adhered in each assay was determined by constructing a standard curve with varying amounts of lysed neutrophils plotted against fluorescent intensity. Routinely, at near maximum binding (20,000 units) approximately 50% of the neutrophils were bound.

Figure 9:
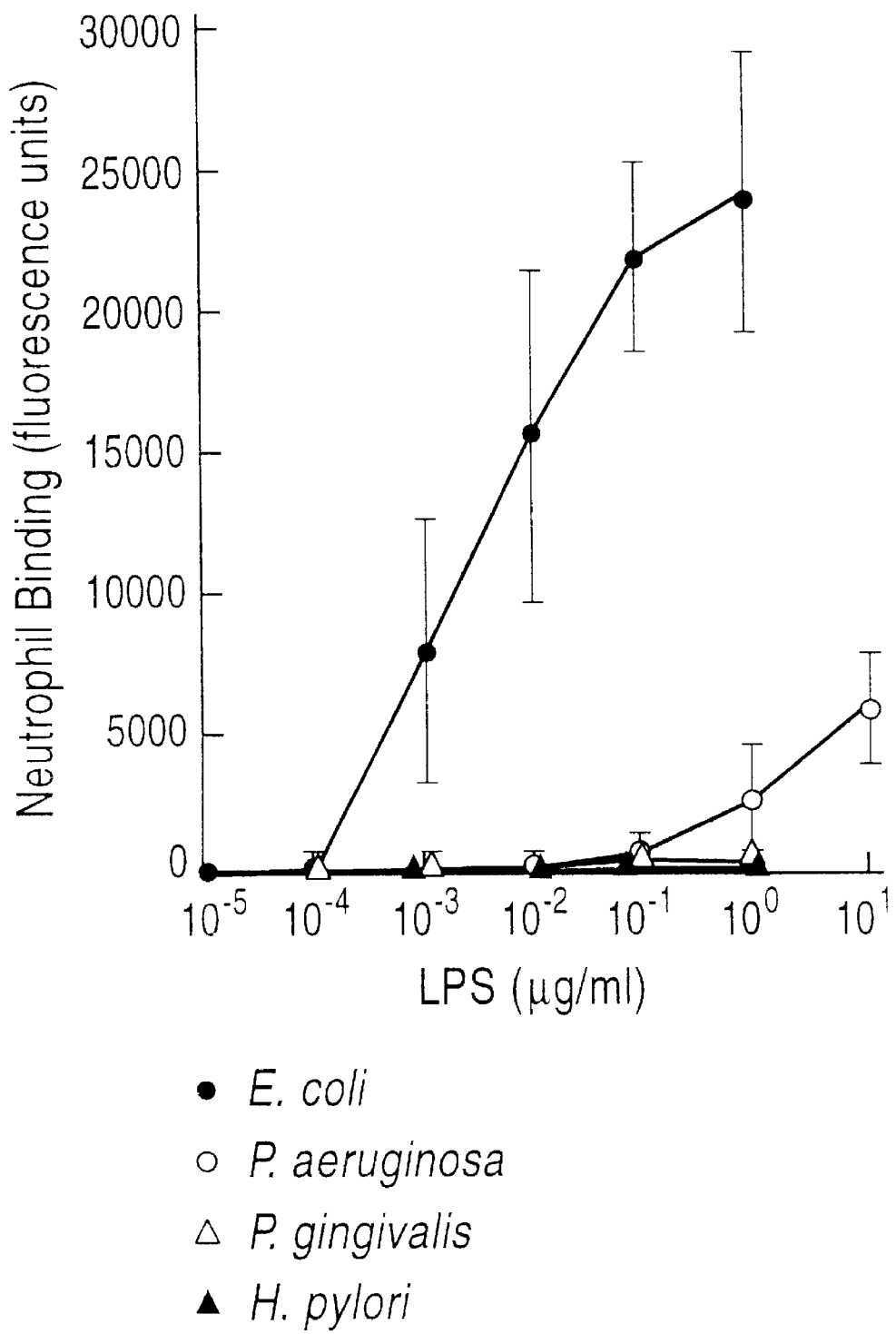
FIG. 9 shows neutrophil adherence to HUVEC treated with different LPS preparations. At maximum binding (2000 units) approximately 50% of the neutrophils were bound.

The results showed that although *E. coli* was a potent inducer of neutrophil adhesion, no adhesion was detected when *P. gingivalis* or *H. pylori* LPS were examined and significantly lower neutrophil adhesion occurred after endothelial cell exposure to *P. aeruginosa* LPS (FIG. 9).

Examination of neutrophil adhesion as opposed to E-selectin expression allowed a determination whether bacterial preparations obtained from *P. gingivalis* or *H. pylori* would promote neutrophil adhesion by E-selectin independent mechanisms. The lack of neutrophil adhesion demonstrates that these organisms could not induce endothelial cell adhesiveness by E-selectin independent mechanisms.

EXAMPLE VII

*P. gingivalis* Inhibits *E. coli*-LPS Induction of Monocyte Chemoattractant Protein from Human Gingival Fibroblasts This Example demonstrates that *P. gingivalis* LPS does not stimulate the production of monocyte chemoattractant protein (MCP-1) from human gingival fibroblasts. MCP-1 is a chemokine, synthesized in response to an inflammatory stimulus and believed to attract leukocytes to the site of inflammation. MCP-1 has been shown to be expressed in normal periodontal tissue and is believed to play a role in the protection of host tissue from damage incurred by the presence of neutrophils.

In these experiments 10 ng/ml of *E. coli* LPS was a potent inducer of MCP-1 mRNA whereas 1 µg of *P. gingivalis* LPS did not result in MCP-1 mRNA expression. In addition, 50 g/ml of *P. gingivalis* LPS was able to block *E. coli* induced MCP-1 expression. These data extend the observations with *P. gingivalis* LPS to include an inhibitory effect on human ingival fibroblasts and chemokine expression.

Primary human gingival fibroblasts (HGF-60) cells were groom in DMEM media supplemented with 10% FBS, sodium pyruvate, glutamine, penicillin and streptomycin. Early passage cultured cells were plated at 1 to $2\times10^6$ cells per 100 mm culture dish and treated with various concentrations of lipopolysaccharides (LPSs) isolated from either *E. coli* (10 ng/ml *E. coli* LPS 011:B4 (Sigma)) or *P. gingivalis* (1000 ng/ml *P. gingivalis* LPS) or mixture of both LPSs, in 2% FCS for 18 to 24 hours. The cells were subsequently harvested for RNA isolation.

Total RNA was isolated by a single step guanidinium thiocyanate-phenol-chloroform method of Chomczynski and Sacchi, *Anal. Biochem.* 162: 156–159 (1987), incorporated herein by reference. Cells were lysed directly on the dish using RNAStat-60 solution, (Tel-Test "B", Inc., Friendswood, Tex.) and the RNA was enriched for mRNA by column purification using RNAStat-30 kit (Tel-Test "B", Inc.) using manufacturer's protocol.

RNA samples (15 µg/lane) were run on 1.0% vertical slab agarose gel containing 6% formaldehyde in 1× MOPS buffer. Gels were run at 70–75 Volts for 4 hours and electrophoresed RNA was transferred to Hybond-N membranes (Amersham Life Sciences) in 20× SSC overnight. Blots were then cross-linked using a UV Stratalinker (Stratagene) and were prehybridized for 4 hours at 42° C. in buffer containing 50% formamide, 4×Denhardts, 5× SSC, 1% SDS, 10 mM Tris-HCl pH 7.5, 50 µg/ml salmon sperm DNA.

Northern blots were hybridized using [$^{32}$p] labeled probe for MCP-1. The probe was obtained by random primed labelling using [$^{32}$p] dCTP by MCP-1 encoding cDNA fragment. Hybridizations were performed at 42° C. overnight in prehybridization buffer containing 1 to $2\times10^6$ cpm $^{32}$p labelled probe per ml. Blots were subsequently washed in 0.2 ×SSC, 0.1% SDS at 65° C., and either autoradiographed or scanned on Molecular Dynamics Phosphorimager. Images were subsequently quantitated.

The results, shown in FIG. 10, demonstrated that *E. coli* LPS produced an intense signal when incubated without *P. gingivalis* LPS. No signal was observed, however, when cells were incubated with *P. gingivalis* LPS (1000 ng/ml). Co-incubation of *E. coli* LPS and 50 ng/ml *P. gingivalis* LPS resulted in the almost complete inhibition of the *E. coli* LPS mediated expression of MCP-1 RNA.

EXAMPLE VIII

*P. gingivalis* Inhibits K Light Chain Expression

This Example demonstrates that the inhibitory effect of *P. gingivalis* LPS includes immunoglobulin producing cells, suggesting that the immunosuppressive effect of such organisms may have wide implications.

The mouse cell line 70 Z/3 is a pre B lymphoma cell line which is frozen in immunoglobulin expression at an early stage, thus it has constitutively expressed µ heavy chain on its surface but does not contain κ light chain. Miller et al., *Mol. Cell. Biol.* 11:4885–4894 (1991), incorporated herein by reference. κ light chain can be induced to be expressed by *E. coli* LPS.

In this experiment 70 Z/3 cells were incubated with the concentrations of *E. coli* LPS indicated on the X axis were co-incubated with 10 µg/ml of *P. gingivalis* LPS. After 18 hrs incubation the expression of κ light chain on the cell surface was examined by fluorescent activated cell sorting (FACS). The results are presented as mean fluorescence.

*P. gingivalis* LPS did not stimulate, but rather, inhibited the ability of *E. coli* LPS to stimulate the expression of κ light chain in mouse 70 Z/3 cells. As shown in FIG. 11, although *E. coli* LPS at 0.1 ng/ml was able to stimulate expression of κ light chain as measured by immunofluorescence, 10 µg/ml of *P. gingivalis* LPS did not result in κ light chain expression. In addition, *P. gingivalis* LPS was able to block *E. coli* induced κ light chain expression when LPS sample were pre-mixed before addition to the cells. These data thus extend the inhibitory effect of *P. gingivalis* LPS to include immunoglobulin producing cells.

EXAMPLE IX

Monoclonal Antibodies Block *P. gingivalis* Mediated Inhibition of E-Selectin and Neutrophil Adhesion This Example demonstrates that monoclonal antibodies directed against *P. gingivalis* LPS can restore near normal E-selectin expression on human endothelial cells exposed to *E. coli* and *P. gingivalis* LPS.

These experiments were performed essentially as described in Example V above, except that monoclonal antibody 7F12 which binds *P. gingivalis* LPS and monoclonal antibody ACE12-3B4 which does not bind *P. gingivalis* LPS were examined. In this experiment, 0.7 μg/ml *P. gingivalis* LPS or 3.3 ng/ml *E. coli* 0111B:4 LPS was added to endothelial cells, either individually or in combination. In addition, monoclonal antibody ACE12-3B4 (which binds to *E. coli* LPS) or monoclonal antibody 7F12 were added to the combination of LPS preparations. Mouse polyclonal sera (from a mouse immunized with *P. gingivalis* LPS) and the prebleed sera were also added to the combination of LPS preparations.

The results showed that when *P. gingivalis* LPS was added to the endothelial cells, little or no stimulation was observed. When *E. coli* LPS was added a significant E-selectin response was obtained. When a combination of *P. gingivalis* LPS and *E. coli* LPS were added the ELISA signal was reduced to near background (0.2). A slight increase in the signal was obtained if a negative control antibody (ACE12-3B4) or mouse polyclonal pre-bleed sera was added to the combination. A further increase in the signal was obtained if a monoclonal antibody to *P. gingivalis* LPA (7F12) or mouse polyclonal sera generated by immunization with *P. gingivalis* LPS was added to the combination. These data demonstrate that antibodies to *P. gingivalis* LPS can inhibit the ability of this LPS to block E-selectin expression.

The ability of the monoclonal antibody to *P. gingivalis* LPS to inhibit the *P. gingivalis*-mediated inhibition of neutrophil binding was then determined. This experiment was performed essentially as described above in Example VI. The neutrophil binding assays were performed with the addition of monoclonal antibodies (purified monoclonal antibodies were added at 10 μg/ml). Monoclonal antibody 4B2 does not bind *P. gingivalis* LPS (it binds to *P. aeruginosa* LPS), monoclonal antibodies 7F12, 6E12, and 5B9 all bind *P. gingivalis* LPS. In this experiment 1 ug/ml *P. gingivalis* LPS was added to endothelial cells or 10 ng/ml *E. coli* 0111:B:4 LPS, either individually or in combination lanes. In addition, monoclonal antibody 4B2 or monoclonal antibodies 7F12, 6E:L2, and 5B9 were added to the combination of LPS preparations.

The results showed that *P. gingivalis* LPS did not promote the adhesion of neutrophils to endothelial cells. In contrast, *E. coli* LPS was able to significantly increase the ability of endothelial cells to bind human neutrophils. When a combination of *P. gingivalis* and *E. coli* LPS was added there was a significant reduction in the ability of the endothelial cells to bind human neutrophils, confirming the *P. gingivalis* LPS can block the ability of *E. coli* LPS to promote neutrophil binding. Further, *H. pylori* LPS is similar to *P. gingivalis* in that it inhibited *E. coli* LPS-mediated stimulation of neutrophil adhesion. When a negative control antibody was added to the *P. gingivalis* and *E. coli* LPS combination no effect on neutrophil binding was observed. In contrast, when monoclonal antibodies to *P. gingivalis* LPS were added to the *P. gingivalis* and *E. coli* LPS combination a significant increase in neutrophil binding was observed. This data demonstrates that monoclonal antibodies to *P. gingivalis* LPS can block the *P. gingivalis* LPS inhibition of neutrophil binding.

EXAMPLE X

*P. gingivalis* Does Not Induce Acute Inflammation In Vivo

This Example demonstrates that *P. gingivalis* does not generate an acute inflammatory response in vivo, in contrast to the acute response resulting from injections of *E. coli* LPS or organisms.

Acute inflammation is characterized by margination of leukocytes in the vasculature and their migration into tissues at the reaction site. This process of leukocyte trafficking involves not only activated leukocytes but activated endothelial cells as well. A mouse model of acute inflammation was established to examine the cellular and temporal pattern of mRNAs expressed for various chemokines and cell adhesion molecules.

In these studies, mice were injected intramuscularly with 0.2 mg of *E. coli* lipopolysaccharide (LPS), a potent inflammatory mediator, and then sacrificed either at 4 or 24 hours. The injected muscles were excised cryosectioned and prepared for in situ hybridization to detect expression of monocyte chemoattractant protein 1 (MCP-1) mRNA, a member of the C-C or β-subfamily of chemokines, for E- and P- selectin mRNAs, the cell adhesion molecules induced on endothelial cells which are critical for leukocyte binding to endothelium and subsequent migration to extravascular tissue sites, or for fibroblast inflammatory chemokine (FIC).

Balb/c mice were injected in the gastrocnemius muscle with 0.2 mg of *E. coli* LPS (0111:B4; Sigma). Control mice received saline. For studies using bacteria, *E. coli* (D471 strain) and *Porphyromonas gingivalis* (strain 33277 *P. gingivalis*) were grown on trypticase agar plates overnight and Brucella blood agar plates anaerobically for five days, respectively. Plated bacteria were suspended to predetermined concentrations and animals were injected with either $10^2$, $10^5$, $10^7$ *E. coli* or $10^6$, $10^8$, $10^{10}$ *P. gingivalis*. The number of cells injected into each animal was confirmed by viable colony counts performed by standard methods.

Mice were sacrificed at either 4 or 24 hours and the muscles excised. For frozen sections, muscles were embedded in OCT compound and cryosectioned. For paraffin sections, muscles were first fixed in 4% paraformaldehyde and then embedded and sectioned.

Probes for in situ hybridization were either ribonucleic acid probes generated from cDNAs or oligonucleotide probes designed from known cDNA sequences. The MCP-1 riboprobe was made from a mouse MCP-1 cDNA in a TA PCR vector (Invitrogen). Template was prepared by PCR directly from the plasmid using Universal and M13 reverse primers. After phenol/chloroform extraction and isopropanol precipitation, the 250 bp fragment was used as a template for transcription by Sp6 RNA polymerase to generate an antisense probe. The IL-1 beta cDNA was obtained from Hoffman-LaRoche, Nutley, N.J. For oligonucleotide probes, a cocktail of probes were used. In the case of E-selectin, two oligos were used: one to the lectin binding domain and another to the EGF region. Oligos for P-selectin were also made to these regions in addition to one of the firm complement domain. Three oligo probes were also made to the coding regions of FIC and MCP-1. Paraffin and frozen sections were prepared for in situ hybridization as described in Sandell et al., *J. Cell Biol.* 114:1307–1319 (1991), and Aigner et al., *Virch. Archiv. B Cell Pathol.* 62:337–345 (1992), incorporated herein by reference.

The results for selectin mRNA expression in muscle which had been injected with *E. coli* LPS were as follows. In situ hybridization of serial sections using oligonucleotide probes (a cocktail of two or three non-overlapping radiolabeled oligonucleotide probes to either E- or P-selectin were used) showed expression of E- and P- selectin mRNAs in endothelial cells from frozen sections of muscle taken 4 hours after the injection of *E. coli* LPS (0.2 mg). Thus, 4 hrs after the induction of inflammation, E- and P-selectin mRNAs were strongly expressed in endothelial cells of capillaries in the endomysium and larger vessels of the perimysium. Strong hybridization for selectin mRNAs was similarly observed in sections of 24 hr inflamed muscle. Muscle injected with PBS as a control showed positive cells only along a narrow tract of tissue probably representing inflammation caused by the insertion of the needle.

The in situ hybridization using a ribonucleic acid probe also showed expression of monocyte chemotactic protein-1 (MCP-1) mRNA in inflammatory cells from frozen sections of muscle taken 4 hours after the injection of $E.\ coli$ LPS (0.2 mg). Frozen section of muscle taken 4 hours after the injection of PBS showed the absence of MCP-1 mRNA and served as a control. In situ hybridization using a cocktail of 3 oligonucleotide probes gave an identical pattern of hybridization. Thus, after 4 hrs, monocyte chemoattractant protein 1 (MCP-1) mRNA was detected in leukocytes using specific radiolabeled ribonucleic acid probe. In these samples, mononuclear but not polymorphonuclear cells, expressing MCP-1 MRNA were abundant throughout the tissue section in the connective tissue septa between muscle bundles (perimysium) and between individual fibers (endomysium). In contrast, after 24 hrs the number of MCP-1 mRNA expressing cells appeared to abate.

This animal model of acute inflammation was then used to compare the action of $E.\ coli$ with that resulting from injections of $P.\ gingivalis$. In situ hybridization in muscle tissue using ribonucleic acid probe showed expression of monocyte chemotactic protein-1 (MCP-1) mRNA in a paraffin section of muscle taken 4 hours after the injection of $10^7$ $E.\ coli$. High magnification showed the expression of MCP-1 mRNA in monocytes but not PMNs. The expression of MCP-1 was observed in only a few cells in a frozen section of muscle taken 4 hours after the injection of $10^{10}$ $P.\ gingivalis$.

The mRNA expression of IL-1 in $E.\ coli$- and $P.\ gingivalis$-injected muscle was also detected by in situ hybridization using ribonucleic acid probe. Expression of IL-1 mRNA was detected in a frozen section of muscle taken 4 hrs after the injection of $10^5$ $E.\ coli$, but the expression of IL-1 was absent in a frozen section of muscle taken 4 hrs after the injection of $10^8$ $P.\ gingivalis$.

mRNA expression of fibroblast inflammatory chemokine (FIC) was also determined in $E.\ coli$- and $P.\ gingivalis$-injected muscle. In situ hybridization using oligonucleotide probes showed expression of FIC mRNA in frozen sections of muscle taken 4 hrs after the injection of $10^5$ $E.\ coli$, whereas the expression of FIC was absent in frozen sections of muscle taken 4 hrs after the injection of $10^8$ $P.\ gingivalis$.

By using this system it was thus demonstrated that monocytes from sections of muscle 4 hrs after an injection of $E.\ coli$ expressed MCP-1 mRNA whereas relatively few cells from muscles injected with even higher doses of $P.\ gingivalis$ expressed this mRNA. Similarly, inflammatory cells from $E.\ coli$ injected muscle also expressed IL-1 and fibroblast inflammatory chemokine (FIC) while those from $P.\ gingivalis$ did not. These data confirmed that $E.\ coli$ induced acute inflammation in the animal but $P.\ gingivalis$ did not. These results are consistent with the in vitro observations and suggests that $P.\ gingivalis$ has developed a cell wall and LPS composition that is poorly recognized by the mammalian inflammatory system.

Although the foregoing invention has been described in some detail by way of illustration and example for purposes of clarity of understanding, it will be obvious that certain changes and modifications may be practiced within the scope of the appended claims.

What is claimed is:

1. A method for modulating the progression of periodontal disease in a mammal, which comprises:

administering to the mammal a compound which inhibits the ability of Porphyromonas gingivalis to inhibit the extravasation of leukocytes from the vascular endothelium to gingival tissues.

2. The method of claim 1, wherein the compound is administered to the periodontium.

3. The method of claim 2, wherein the compound is administered by mouthwash, aerosol, paste or salve.

4. The method of claim 1, wherein the compound inhibits the ability of $P.\ gingivalis$ lipopolysaccharide to inhibit the extravasation of leukocytes from the vascular endothelium to gingival tissues.

5. The method of claim 4, wherein the compound is a monoclonal antibody that binds $P.\ gingivalis$ lipopolysaccharide.

6. The method of claim 4, wherein the compound degrades the lipopolysaccharide of $P.\ gingivalis$.

7. The method of claim 1, wherein the compound is purified acyloxyacyl hydrolase.

8. The method of claim 1, wherein the compound is targeted to the periodontium by an antibody that binds to P- or E-selectin.

9. The method of claim 8, wherein the antibody is a bifunctional antibody which binds to P- and E-selectin.

10. The method of claim 9, wherein the compound is directly linked to the antibody.

11. A composition for inhibiting gram-negative bacterial infection, the composition comprising a pharmaceutical carrier and a binding polypeptide which binds to lipopolysaccharide of $P.\ gingivalis$ and which inhibits the ability of said $P.\ gingivalis$ lipopolysaccharide to suppress selectin expression by host endothelial cells.

12. The composition according to claim 11, wherein said binding polypeptide is a monoclonal antibody.

13. The composition according to claim 12, wherein said monoclonal antibody is a substantially human antibody.

* * * * *